United States Patent [19]

della Valle et al.

[11] Patent Number: 5,442,053

[45] Date of Patent: * Aug. 15, 1995

[54] SALTS AND MIXTURES OF HYALURONIC ACID WITH PHARMACEUTICALLY ACTIVE SUBSTANCES, PHARMACEUTICAL COMPOSITIONS CONTAINING THE SAME AND METHODS FOR ADMINISTRATION OF SUCH COMPOSITIONS

[75] Inventors: Francesco della Valle, Padova; Aurelio Romeo, Rome; Silvana Lorenzi, Padova, all of Italy

[73] Assignee: Fidia, S.p.A., Abano Terme, Italy

[ * ] Notice: The portion of the term of this patent subsequent to Jul. 25, 2006 has been disclaimed.

[21] Appl. No.: 931,949

[22] Filed: Aug. 19, 1992

Related U.S. Application Data

[63] Continuation of Ser. No. 452,681, Dec. 19, 1989, Pat. No. 5,166,331, which is a continuation of Ser. No. 756,824, Jul. 19, 1985, abandoned, which is a continuation-in-part of Ser. No. 719,113, Apr. 2, 1985, abandoned, and Ser. No. 669,431, Nov. 8, 1984, abandoned, and a continuation-in-part of Ser. No. 425,462, Sep. 28, 1982, Pat. No. 4,593,091.

[30] Foreign Application Priority Data

Oct. 10, 1983 [IT] Italy .................................. 49143/83
Oct. 9, 1984 [IT] Italy .................................. 48979/84
Apr. 2, 1985 [IT] Italy .................................. 47924/85

[51] Int. Cl.$^6$ ............................................ C07H 5/04
[52] U.S. Cl. ................................. 536/55.1; 514/54; 514/420; 514/576; 514/777; 514/912; 424/78.05
[58] Field of Search .................. 536/55.1; 514/54, 777, 514/420, 576, 912; 424/78.05

[56] References Cited

U.S. PATENT DOCUMENTS

| | | |
|---|---|---|
| 2,583,096 | 7/1952 | Hadidian et al. . |
| 3,396,081 | 8/1968 | Billek ................................. 536/35.1 |
| 3,436,454 | 4/1969 | Nouvel . |
| 3,792,164 | 2/1974 | Bechtold ............................. 424/273 |
| 3,845,201 | 10/1974 | Haddad et al. ....................... 424/180 |
| 3,870,791 | 3/1975 | Haddad et al. ....................... 424/22 |
| 3,887,703 | 6/1975 | Manoussos et al. . |
| 4,003,991 | 1/1977 | Krohn et al. ......................... 424/81 |
| 4,045,558 | 8/1977 | Smith et al. ......................... 424/232 |
| 4,061,722 | 12/1977 | Bodor ................................. 424/273 |
| 4,141,973 | 2/1979 | Balazs . |
| 4,255,415 | 3/1981 | Chrai et al. ......................... 424/78.1 |
| 4,271,143 | 6/1981 | Schoenwald et al. ................ 424/78 |
| 4,272,522 | 6/1981 | Balazs . |
| 4,303,676 | 12/1981 | Balazs . |
| 4,328,803 | 5/1982 | Pape .................................. 514/54 |
| 4,500,676 | 2/1985 | Balazs et al. ........................ 424/273 |
| 4,517,295 | 5/1985 | Bracke et al. ........................ 536/123 |
| 4,593,091 | 6/1986 | della Valle et al. ................... 536/53 |
| 4,851,521 | 7/1989 | della Valle et al. ................... 424/443 |
| 5,166,331 | 11/1992 | della Valle et al. ................... 536/55.1 |
| 5,202,431 | 4/1993 | della Valle et al. ................... 424/423 |

FOREIGN PATENT DOCUMENTS

| | | |
|---|---|---|
| 8430806 | 2/1985 | Australia . |
| 138572 | 4/1975 | European Pat. Off. . |
| 0136782 | 4/1985 | European Pat. Off. . |
| 066283 | 12/1992 | European Pat. Off. . |
| 2364373 | 7/1975 | Germany . |
| 57-183707 | 11/1982 | Japan . |
| 1283892 | 8/1972 | United Kingdom . |
| 2099826 | 12/1982 | United Kingdom . |
| 8403302 | 8/1984 | WIPO . |

OTHER PUBLICATIONS

Deguchi et al "Binding of Aminoglycoside Antibiotics to Acidic Mucopolysaccharides", Journal of Antibiotics, Feb. 1978, vol. 31, pp. 150–155.

M. Walther, Minerva Gynecologica, 33, 497–499 (1981).

P. Surtoli et al., Giornale Italiano di Dermatologia, 45(8), 468–471 (1970).

R. O. Cravioto et al., Science, 111, 520–521 (1950).

E. A. Balazs, Chemistry and Molecular Biology of the Intercellular Matrix, III, 1241–1253 (1970).

N. W. Rydell et al., Clinical Orthopaedics and Related Research, 80, 25–32 (1971).

W. McIlwraith, Journal of the American Veterinary Medical Association, 239–250 (1982).

S. P. Vilesov et al., Klin Khir, 9, p. 71 (1970).

(List continued on next page.)

Primary Examiner—Nathan M. Nutter
Attorney, Agent, or Firm—Birch, Stewart, Kolasch & Birch

[57] ABSTRACT

Two pharmaceutically useful fractions of hyaluronic acid are obtained comprising a first fraction with a molecular weight between 50,000 and 100,000 which is useful for wound healing, and a second fraction having a molecular weight between 500,000 and 730,000 which is useful for intraocular and intraarticular injections.

In addition, pharmaceutical preparations for topical administration are provided containing a pharmacologically active substance together with hyaluronic acid or a molecular weight fraction thereof. The hyaluronic acid may be in the form of the free acid or may be a salt with an alkali or alkaline earth metal, magnesium, aluminum or ammonium, or in the form of a salt with one or more pharmacologically active substances.

60 Claims, 1 Drawing Sheet

OTHER PUBLICATIONS

Nizolek et al., *The Cornell Veterinarian*, 71(4) 355–375 (1981).
Weirich et al., *Dermatologica*, 152(2) 87–99 (1976).
The New Encyclopaedia Britannica, vol. VIII, 1977:102.
Mizushima, *Nippon Rinsho*, 26(1) 61–65 (1968).
Katsu et al., *Nippon Rinsho*, 26(1) 89–95 (1968).
Vasil'ev et al., *Antibiotiki*, 21(3):238–242 (1976).
Shchekotova, *Antibiotiki*, 17(2) 134–137 (1982).
Haydon, *Klin Monatsbl. Augenheilkd*, 183(3):213–215 (1983).
Stavri et al., *Rev. Med. Chir. Soc. Med. Nat. Iasi.*, 81(1):133–136 (1981).
Leibowitz et al., *Curr. Eye Res.* 1(5)259–266 (1981).
Darougar et al., *Br. J. Ophthalmol.* 64(1):37–42 (1980).
Genee et al., *Ophthalmologica*, 184(2) 92–96 (1982).
Sakaguchi et al., *Nippon Ganka Kiyo*, 20(7):743–746 (1969).
McGuinness, *Med. J. Aust.*, 140(6):383 (1984).
Nakatsue, *Nippon Ganka Gakkai Zasshi* 75(5):1244–1247 (1971).
Norn, *Ugeskr. Laeger*, 137(42):2458–2460 (1975).
Nielson et al., *Acta Ophthalmol.*, 57(3):418–424 (1979).
Fisher et al., *J. Infect. Dis.*, 147(1):164 (1983).
Bird et al., *Br. J. Ophthalmol.*, 64(3):191–200 (1980).
Tabbara et al., *Am. J. Ophthalmol.*, 98(3):378–380 (1984).
Hung et al., *Br. J. Ophthalmol.*, 68(3):192–195 (1984).
Kabuni et al., *Bull. Soc. Belge. Ophtalmol.*, 201:99–104 (1982).
Szasne Zacsko et al., *Acta. Pharm. Hung.*, 53(4):150–153 (1983).
Brian et al., *J. Pharm. Sci.*, 63(4):633–635 (1974).
Springer et al., *Pharmazie*, 36(10):706–708 (1981).
Salminen et al., *Exp. Eye Res.*, 38(2):203–206 (1984).
Merte et al., *Klin. Monatsbl. Augenheilkd* 184(3):227–232 (1984).
Schmitz et al., *Fortschr. Ophthalmol.*, 79(4):374–378 (1982).
Dhir et al., *Indian J. Ophthalmol.*, 29(3):229–233 (1981).
Nielsen, *Acta Ophthalmol.*, 59(4):495–502 (1981).
Bonomi et al., *Albrecht Von Graefes Arch. Klin. Exp. Ophthalmol.*, 217(3):175–181 (1981).
Ichigashira et al., *Steroids*, 32(5) 615–628 (1978).
Egorov et al., *Oftalmol. Zh.*, 35(4) 212–215 (1980).
Niebroj et al., *Klin. Oczna*, 46(3) 301–303 (1976).
M. Walther, Minerva Gynecologica, 33, 497–499 (1981).
P. Surtoli et al., Giornale Italiano di Dermatologia, 45(8), 468–471 (1970).
R. O. Cravioto et al., Science, 111, 520–521 (1950).
E. A. Balazs, Chemistry and Molecular Biology of the Intercellular Matrix, III, 1241–1253 (1970).
N. W. Rydell et al., Clinical Orthopaedics and Related Research, 80, 25–32 (1971).
W. McIlwraith, Journal of the American Veterinary Medical Association, 239–250 (1982).
S. P. Vilesov et al., Klin Khir, 9, p. 71 (1970).
Balazs and Laurent, Chem. & Mol. Biol. of the Intercellular Matrix, 2 (1970) 703–732.
Fraser et al., Chem. Abst., vol. 87, No. 21 (21 Nov. 1977), 170 No. 163114a.
Swann, Biochimica et Biophysica Acta, vol. 160, 1968.
Chemical Abstracts, vol. 102, No. 16, Resume No. 137591n.
Chemical Abstracts, vol. 68, No. 7, Resume No. 27273q.
Chemical Abstracts, vol. 80, No. 15, Resume No. 79756j.
Chemistry and Industry, Feb. 12, 1955, pp. 168–169.
Takashi et al., The Journal of Antibiotics vol. 31 (1978) pp. 150–155.
Cleland Chemical Abstracts, vol. 76 (1972) No. 43073q "Molecular Weight Distribution in Hyaluronic Acid".
Laurent et al., Chemical Abstracts vol. 98 (1983) No. 211813f "The Molecular Weight of Hyaluronate on the Aqueous Tumor."
Shimada et al., J. Biochem. vol. 31 (1977) pp. 79–91 "Molecular Weight of Hyaluronic Acid from Rabbit Skin".
Barron et al., American Journal of Ophthalmology vol. 100 (1985) pp. 377–389 "Comparison of the Effects of Viscoat and Heater."
Swann, *Biochem. Biophys. Acta.* vol. 156, 1968 pp. 17–30.
Popovici et al., *Chemical Abstracts* vol. 77, 1972 No. 394 m, p. 60.
Abatangelo et al. *Exp. Cell. Res.* vol. 137, 1982 pp. 73–78.
VISCOAT Trademark Principal Register.

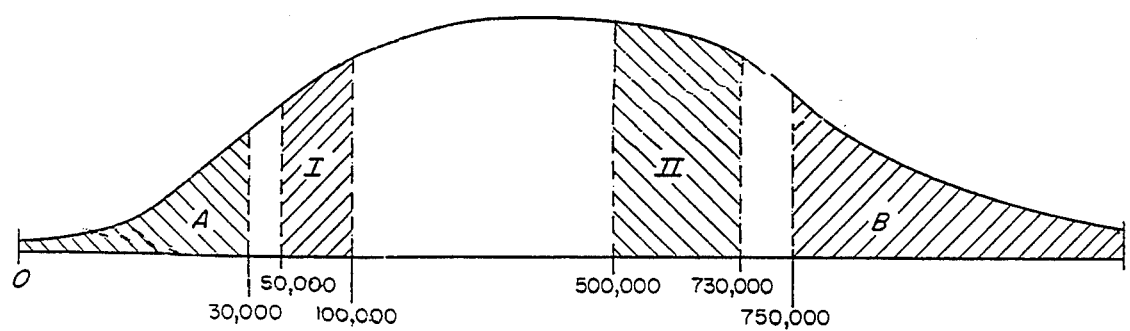
AVERAGE MOLECULAR WEIGHT OF HYALURONIC ACID

SALTS AND MIXTURES OF HYALURONIC ACID WITH PHARMACEUTICALLY ACTIVE SUBSTANCES, PHARMACEUTICAL COMPOSITIONS CONTAINING THE SAME AND METHODS FOR ADMINISTRATION OF SUCH COMPOSITIONS

This application is a continuation of application Ser. No. 07/452,681, filed on Dec. 19, 1989, now U.S. Pat. No. 5,166,331, which is a continuation of application Ser. No. 756,824, filed Jul. 19, 1985, now abandoned, which is a continuation-in-part of U.S. application Ser. No. 719,113 filed on Apr. 2, 1985, now abandoned application Ser. No. 669,431 filed Nov. 8, 1984, now abandoned, and of application Ser. No. 06/425,462, filed Sep. 28, 1982 and now U.S. Pat. No. 4,593,091, the entire contents of which are hereby incorporated by reference.

BACKGROUND AND FIELD OF THE INVENTION

This invention relates to specific molecular weight fractions of hyaluronic acid (hereinafter referred to as "HA" or HY) which have therapeutic applications and which are non-inflammatory when utilized. One of the HA fractions of this invention is particularly useful for facilitating wound healing, while the second HA fraction is particularly useful for intraocular use to substitute for endobulbar fluids or for intraarticular injection for use in treating damaged bone joints.

The invention further relates to the use of the HA fractions as vehicles for ophthalmic drugs. The use of HA as a vehicle provides a formulation compatible with the corneal epithelium and enhances the activity of some ophthalmic drugs.

Furthermore, the invention relates to new medicaments for topical use and more precisely to medicaments containing:

1. an active pharmacological substance or an association of pharmacological substances, either active or suitable for topical administration and
2. a vehicle made of hyaluronic acid or a molecular weight fraction of the same or a salt thereof with an alkaline metal, an alkaline earth metal, with magnesium, aluminum, ammonium or ammonium substitute, and optionally additional ordinary excipients used in pharmaceutical preparations for topical use, therapeutic use or preventive purposes.

Hyaluronic acid is a naturally occurring heteropolysaccharide consisting of alternating residues of D-glucuronic acid and N-acetyl-D-glucosamine. HA is a linear polymer of high molecular weight, generally up to about 8 to 13 million, and has been found in cell coats, pericellular gels, the extracellular ground substance of connective tissues of vertebrates, in the synovial fluid in joints, in the endobulbar fluids or vitreous humor of the eye, in human umbilical cord tissue, in rooster combs and in some bacteria.

Previous investigations on HA include the work of Balazs, U.S. Pat. No. 4,141,973, directed to a fraction of HA useful for replacing endobulbar fluids, as well as other therapeutic applications. This patent, however, is specifically directed to an HA fraction having an average molecular weight greater than about 750,000, and preferably greater than about 1,200,000. Balazs specifically teaches that fractions of HA having an average molecular weight of less than 750,000 are not therapeutically useful because of their inflammatory activity. These lower molecular weight fractions of HA are discarded by Balazs. However, this results in discarding about 90% of the total amount of available HA obtainable from the source tissues, resulting in a use of only a small amount (about 10%) of the available HA.

In addition, hyaluronic acid has been widely useful in medicine and a cosmetic use is also being considered (see for example the article by Balazs et al. in "Cosmetics & Toiletries" Italian edition No. 5/84 with relative references). It has especially been used as a therapeutic agent in therapies for arthropathies, such as in the veterinary field to cure arthritis in horses (see Acta Vet. Scand. 167, 379 (1976)). Hyaluronic acid and fractions thereof have been used in ophthalmic surgery as therapeutic, auxilliary and substitutive agents for natural organs and tissues (see for example E. A. Balazs et al. "Modern Problems in Ophthalmology", 10, 3 (1970), E. B. Strieff, S. Karger, eds. Basel and Balazs et al. "Viscosurgery and the Use of Sodium Hyaluronic During Intraocular Lens Implantation" Paper presented at the International Congress and First Film Festival on Intraocular Implantation, Cannes, 1979).

There is also at present particular interest in obtaining ophthalmic vehicles which do not cause sensitization phenomena in the cornea and which guarantee perfect tolerability, thereby forming efficient vehicles for drugs. In this context much attention has been placed on the use of natural biological molecules as possible vehicles for ophthalmic drugs as they ensure a high level of tolerability and compatibility with the corneal epithelium.

Contrary to the teachings of Balazs, the present inventors have discovered that lower molecular weight fractions of HA do indeed have useful pharmaceutical activity. Thus, according to the present invention, about 80% of the HA obtainable from various sources is utilized. In particular, the present inventors have discovered one fraction of HA which is useful for stimulating wound healing, and a second fraction of HA which is useful for intraocular injections to substitute for the endobulbar liquids in the eye and for intraarticular injections as a treatment for damaged joints. Moreover, the inventors have discovered that hyaluronic acid and the molecular weight fractions of HA are useful as a vehicle for drugs, particularly ophthalmic and topically administered drugs.

OBJECTS AND SUMMARY OF THE INVENTION

It is, therefore, one object of the present invention to provide specific well defined fractions of hyaluronic acid having pharmaceutical applications and without inflammatory activity.

It is another object of the present invention to provide a fraction of HA which is useful for stimulating wound healing.

It is another object of the invention to provide a fraction of HA which is useful for intraocular and intraarticular injections for replacing the endobulbar liquids in the eye and for treating damaged bone joints, respectively.

It is a further object of the present invention to provide fractions of HA which are therapeutically useful and which permit the use of a high percentage of the available HA that can be obtained from source tissues.

It is still a further object of the present invention to provide a method for obtaining specific fractions of HA depending upon the average molecular weight for differing therapeutic applications.

It is another object of the present invention to provide ophthalmic solutions having excellent toleration to the cornea.

It is another object of the invention to provide an opthalmic solution containing hyaluronic acid as the vehicle whereby an efficient drug vehicle is provided.

It is a further object of the invention to enhance the biological activity of ophthalmic drugs by admixing the drugs with a vehicle comprising hyaluronic acid.

These and other objects of the present invention are accomplished by obtaining two specific well defined fractions of hyaluronic acid. According to the invention, one fraction of HA having an average molecular weight of between about 50,000 to about 100,000 is useful for wound healing, and a second fraction of HA having an average molecular weight of about 500,000 to about 730,000 is useful for intraocular and intraarticular injections. In addition, the hyaluronic acid fractions are utilized as a drug vehicle in ophthalmic compositions. The hyaluronic acid containing compositions have excellent tolerability to the cornea and enhance the activity levels of some ophthalmic drugs.

BRIEF DESCRIPTION OF THE DRAWING

FIG. 1 is a graph showing the different fractions of hyaluronic acid which have been identified by the present inventors.

DETAILED DESCRIPTION OF THE INVENTION

I. Molecular Weight Fractions of HA

As discussed above, previous investigations of HA, as exemplified by the Balazs patent, have been directed to utilizing high molecular weight fractions with an average molecular weight of greater than 750,000. The present inventors have isolated and characterized two new fractions of HA, one having a low molecular weight and another having a medium ranged average molecular weight, which are of a high degree of purity and do not have inflammatory activity. These new fractions of HA can be obtained from various connective tissues which contain extractable amounts of hyaluronic acid. The specific fractions of the invention are differentiated and separated according to molecular filtration techniques.

The first fraction isolated by the inventors has been named HYALASTINE, and has an average molecular weight of from about 50,000 to about 100,000. This HYALASTINE fraction has been determined to be suitable for therapeutic, veterinary and human use because of its wound healing activity. The second fraction isolated by the inventors has been labelled HYALECTIN, and has an average molecular weight of about 500,000 to about 730,000. This HYALECTIN fraction is suitable for use in ocular surgery as a substitute for endobulbar liquids and for veterinary and human therapy in traumatic and degenerative diseases of the joints.

HYALASTINE can be administered either as an intradermal injection or it can be applied as a topical agent for wound healing. HYALECTIN, on the other hand, is suitable for intraocular and intraarticular injection.

The present inventors have made intensive studies on the various fractions of HA and, in a significantly more precise way than previously accomplished, have specifically determined the therapeutically useful fractions of HA and the inflammatory and non-useful fractions of HA. As a result of these studies, the present inventors have identified and investigated two specific characteristics of HA fractions, namely cell mobilization activity and intrinsic viscosity. The wound healing process in animals is facilitated by cellular mobilization, and particularly the mobilization of fibroblasts. On the other hand, cellular mobilization or proliferation activity (i.e., mytosis) is to be avoided in cases of surgery inside the ocular globe. This is particularly true in operations to correct retinal detachment where an increased rate of healing may cause harmful affects.

The intrinsic viscosity is also an important parameter to be considered in determining the utility of a fraction of HA. A fraction having a high intrinsic viscosity is useful for surgical uses, in the therapy of diseases of the joints of a traumatic and degenerative nature, and for replacing endobulbar liquids. On the other hand, high viscosity is an undesirable characteristic for fractions to be utilized as drugs for facilitating wound healing. In fact, fractions to be utilized in wound healing should have low viscosity so as to be more easily used in practical application.

The HYALASTINE fraction identified by the present inventors has been determined to have good mobilization or cell proliferation activity, and low viscosity characteristics. Accordingly, HYALASTINE has the characteristics desirable for a material useful in promoting wound healing. The same characteristics make the HYALASTINE fraction undesirable for use in intraocular or intraarticular-injection treatments.

The HYALECTIN fraction identified by the inventors has been determined to have negligible cell mobilization or proliferation activity, while at the same time having high viscosity. These characteristics, therefore, make the HYALECTIN fraction useful for intraocular and intraarticular injection treatments. But, on the other hand, HYALECTIN is not useful for wound healing treatments since this fraction does not exhibit cell mobilization activity.

In isolating useful fractions of hyaluronic acid, it is also important to obtain those fractions which do not have inflammatory activity. The Balazs patent noted above teaches that in order to obtain hyaluronic acid fractions without inflammatory activity, fractions having an average molecular weight of more than 750,000 must be utilized exclusively. Thus, Balazs discards the fractions having less than 750,000 average molecular weight as being non-useful because of inflammatory activity. Contrary to the teachings of Balazs, the present inventors have found that the inflammatory activity attributed by Balazs to fractions having an average molecular weight of less than 750,000 is actually due to impurities having an average molecular weight of less than 30,000. Thus, the present invention provides a method which comprises a series of molecular filtration techniques associated with chemical methods by which the inflammatory fraction having a molecular weight of less than 30,000 can be eliminated.

By the methods of the invention, it is possible to obtain useful fractions of hyaluronic acid having no inflammatory activity which, when considered together, constitute a total yield of about 80% of the total hyaluronic acid available from the particular starting materials. This 80% yield of-the available hyaluronic acid comprises a combined fraction which is a combination of the HYALECTIN and HYALASTINE fractions and which has an average molecular weight of from about 250,000 to about 350,000. More specifically, the HYALECTIN fraction is Obtained in a yield of about 30% of the available HA and the HYALASTINE fraction is obtained in a yield of about 50% of the available HA from the starting tissues. This factor is an important improvement over the process of the Balazs patent discussed above in that the present inventors have discovered that significantly increased amounts of the available hyaluronic acid are pharmaceutically useful. By utilizing only the fraction having an average molecular weight of greater than 750,000, the Balazs process obtains a yield of only about 10% of the original hyaluronic acid available from animal organs, and discards about 90% of the available hyaluronic acid. Thus, according to the present invention, the usefulness of the total hyaluronic extract has been greatly increased. A comparison of the relative yields of the extraction of various fractions of hyaluronic acid is presented below in Table 1.

TABLE 1

| Type of Hyaluronic Acid | g per 100 g of fresh tissue | % | Reference |
| --- | --- | --- | --- |
| Total hyaluronic acid from rooster combs | 0.8 | 100 | Swann D. A. 1968, Biochim, Biophys. Acta 156, 17–29 |
| HA (Balazs type) | 0.08 | 10 | U.S. Pat No. 4,141,973 |
| HYALECTIN + HYALASTINE | 0.6 | 80 | present invention |
| HYALECTIN | 0.2 | 30 | present invention |
| HYALASTINE | 0.4 | 50 | present invention |
| Inflammatory fraction | 0.16 | 20 | present invention |

The isolation and characterization of these two distinct fractions of HA is important because by this discovery it is possible to obtain useful fractions of hyaluronic acid having no inflammatory activity which, when considered together, constitute a total yield of about 80% of the total hyaluronic acid available from the particular starting materials. This 80% yield of the available hyaluronic acid comprises a combined fraction which is a combination of the HYALECTIN and HYALASTINE fractions and which has an average molecular weight of from about 250,000 to about 350,000. More specifically, the HYALECTIN fraction is obtained in a yield of about 30% of the available HA and the HYALASTINE fraction is obtained in a yield of about 50% of the available HA from the starting tissues.

The characterization of the HYALECTIN and HYALASTINE fractions is further important because the preparation procedure is for these fractions eliminates the low molecular weight HA fraction having an average molecular weight of less than 30,000 which has been found to be the fraction which causes the inflammatory activity previously noted with various extracts of HA when administered in vivo.

FIG. 1 graphically shows the different HA fractions which the present inventors have identified. The solid bell-shaped curve of FIG. 1 represents the approximate distribution of the HA fractions available from a starting tissue. Area "B" in FIG. 1 represents the HA fraction identified by Balazs in U.S. Pat. No. 4,141,973 as being pharmaceutically useful. Areas "A", I and II in FIG. 1 Are the fractions identified by the present inventors—area A being the inflammatory fraction having an average-molecular weight less than 30,000; area I being the HYALASTINE fraction; and area II being the HYALECTIN fraction. From this graph, it can be seen that the Balazs method discards the large majority of available extractable HA by eliminating the HA fractions having an average molecular weight of less than 750,000. The present invention, on the other hand, permits the pharmaceutical use of a large proportion of available HA since the low molecular weight hyaluronic acid fraction having an average molecular weight of less than 30,000 causes the inflammatory activity which previous investigators have noted with various extracts of HA.

The present inventors have discovered that a large percentage of available HA can, in fact, be utilized for therapeutic purposes if separated according to the teachings of this invention depending upon the particular therapeutic application. While the Balazs patent specifically teaches the use of only about 10% of the available HA, the present invention permits the use of about 80% of the available HA either in the form of the HYALASTINE fraction for wound healing applications, or in the form of the HYALECTIN fraction for intraocular and intraarticular applications, or in the form of a combined HYALASTINE and HYALECTIN fraction which can also be used for wound healing applications.

The chemical and physical characteristics of the identified fractions have also been investigated by the present inventors, and these characteristics are summarized in Table 2.

A. Methods of Preparing Molecular Weight Fractions of HA

The following describes exemplary procedures for obtaining the differentiated HA fractions.

EXAMPLE I

Method for obtaining a mixture of HYALASTINE and HYALECTIN fractions without inflammatory activity:

Hen crests, either fresh or frozen (3000 g), are minced in a meat mincer and then carefully homogenized in a mechanical homogenizer. The resulting paste is placed in an AISI 316 stainless steel container or in a glass container with 10 volumes of anhydrous acetone. The entire content is then agitated for 6 hours at a speed of 50 g/minute and left to separate for 12 hours, after which the acetone is syphoned off and discarded.

This extraction process is repeated until the discarded acetone has reached the correct humidity level (Karl-Fischer method).

The resulting substance is then centrifuged and vacuum dried at a suitable temperature for 5–8 hours. With this process, approximately 500–600 g of dry powder is obtained from the hen crests.

300 g of the dry powder is then submitted to an enzymatic digestion process with papain (0.2 g) through a buffered aqueous medium with a phosphate buffer in the presence of a suitable quantity of cysteine hydrochloride. This mixture is then agitated for 24 hours at 60 g/minute at a constant temperature of 60°–65° C. This whole mass is cooled to 25° C. adding 60 g of Celite$^{(R)}$ and the agitation is maintained for an additional hour.

The resulting mixture is filtered until a clear liquid is obtained. This clear liquid then undergoes molecular ultrafiltration by means of membranes with a molecular exclusion limit of 30,000 to retain on the membrane those molecules with a molecular weight of greater than 30,000. Five to six original volumes are ultrafiltered and, at the same time, distilled water is three volumes of ethanol (95%). The precipitate is collected by centrifugation and the supernatant discarded. The precipitate is dissolved in 1 liter of 0.1M sodium chloride solution and the precipitation procedure is

TABLE 2

| | CHEMICAL AND PHYSICAL CHARACTERISTICS | | | | |
|---|---|---|---|---|---|
| Fractions | M.W. | Dynamic viscosity at 20° C. | Titer in hyaluronic acid of % dry powder | Content in proteins as bovine albumin | Content in sulphurated mucopolysaccharides |
| HYALASTINE + HYALECTIN | 250,000–340,000 | 100 mP.s. (conc. 1% w/v) | >96%[a] | <0.5% | <1% |
| HYALASTINE | 50,000–100,000 | 600 mP.s. (conc. 5% w/v) | >96% | <0.5% | <1% |
| HYALECTIN | 500,000–730,000 | 170 mP.s. (conc. 1% w/v) | >96% | <0.5% | <1% |

[a]Values presented represent the titer in HA after elimination in water. For example, a titer of 96% represents that, after elimination of water, the powder contains 4% impurities and 96% hyaluronic acid.

continually added to the product. The addition of distilled water is suspended and the product is ultrafiltered until it is reduced to one-third of its original volume.

The residue liquid is rendered 0.1M by adding sodium chloride and the temperature is brought to 50° C. 45 g of cetylpyridinium chloride is added while the product is being agitated at 60 g/minute. This mixture is agitated for 60 minutes, after which 50 g of Celite[(R)] is added. Under agitation the temperature of the product is reduced to 25° C. and the precipitate formed is collected by means of centrifugation. The precipitate thus obtained is suspended in a 0.01M solution of sodium chloride (5 liters) containing 0.05% cetylpyridinium chloride. It is agitated for a further 60 minutes at 50° C. The temperature is lowered to 25° C. and the precipitate centrifuged.

The washing process is then repeated three times and the precipitate finally gathered into containers holding 3 liters of a 0.05M solution of sodium chloride containing 0.05% of cetylpyridinium chloride. This is agitated at 60 g/minute for 60 minutes and maintained at a constant temperature of 25° C. for a period of 2 hours. The lipid supernatant is eliminated by means of centrifugation.

The procedure is thus repeated several times with a 0.1M sodium chloride solution containing 0.05% of cetylpyridinium chloride. The mixture is centrifuged and the supernatant discarded. The precipitate is dispersed in a 0.30M sodium chloride solution containing 0.05% of cetylpyridinium chloride (3 1). The mixture is agitated and both the precipitate and the clear liquid are gathered. Extraction is repeated on the precipitate an additional 3 times, each time using 0.5 liters of the same aqueous solution.

Finally, the residue precipitate is eliminated and the clear liquids united in a single container. The temperature of the liquid is increased to 50° C. while agitating. The liquid is then brought to 0.23M with sodium chloride. 1 g of cetylpyridinium chloride is added and agitation maintained for 12 hours. The mixture is cooled to 25° C. then filtered, first through Celite[(R)] packs and then through a filter (1μ).

The resultant mixture then undergoes a further molecular ultrafiltration through membranes with a molecular exclusion limit of 30,000, ultrafiltering 3 original volumes with the addition of 0.33M sodium chloride solution. The addition of the sodium chloride solution is suspended and the volume of the liquid reduced to a quarter of its original volume.

The solution thus concentrated is precipitated under agitation (60 g/minute) at a temperature of 25° C. with repeated with three volumes of 95% ethanol.

The precipitate is gathered and washed, first with 75% ethanol (three times), then with absolute ethanol (three times) and thirdly with absolute acetone (three times).

The product thus obtained (HYALASTINE+HYALECTIN fraction) has an average molecular weight between 250,000 and 350,000.

The hyaluronic acid yield is equal to 0.6% of the original fresh tissue.

EXAMPLE II

Method for obtaining the HYALASTINE fraction from the mixture obtained by the method described in Example I:

The mixture obtained by the method described in Example I is dissolved in pyrogen free distilled water in proportions of 10 mg of product in 1 ml of water. The solution thus obtained undergoes molecular ultrafiltration through membranes with a molecular exclusion limit of 200,000 with a concentration technique and without addition of water on the membrane. During the ultrafiltration process through membranes with an exclusion limit of 200,000, molecules with molecular weight greater than 200,000 will not pass, whereas smaller molecules will pass through the membrane along with the water. During the filtration process no water is added in the compartment above the membrane; therefore, the volume in this compartment will decrease, along with an increase in the concentration of molecules with M.W. over 200,000. It is then ultrafiltered until the volume on the membrane is reduced to 10% of the initial volume. Two volumes of pyrogen free bidistilled water are added and the solution is again ultrafiltered until the volume is reduced to one-third. The operation is repeated another two times.

The solution which passes through the membrane is brought to 1.0M with sodium chloride and then precipitated with four volumes of ethanol at 95%. The precipitate is washed three times with 75% ethanol and then vacuum dried.

The product thus obtained (HYALASTINE fraction) has an average molecular weight between 50,000 and 100,000.

The hyaluronic acid yield is equal to 0.4% of the original fresh tissue.

EXAMPLE III

Method of obtaining HYALECTIN fraction:

The concentrated solution, gathered into a container from the ultrafiltration membrane with a molecular exclusion limit of 200,000 described in Example II, is diluted with water until a solution containing 2 mg/ml of hyaluronic acid is obtained, as determined by quantitative analysis based upon an assay of glucuronic acid.

The solution is brought to 0.1M in sodium chloride and then precipitated with 4 volumes of 95% ethanol. The precipitate is washed three times with 75% ethanol and then vacuum dried.

The product thus obtained (HYALECTIN fraction) has an average molecular weight between 500,000 and 730,00. This corresponds to a specific hyaluronic acid fraction of defined molecular chain length of about 2,500 to 3,500 saccharide units with a high degree of purity.

The hyaluronic acid yield is equal to 0.2% of the original fresh tissue.

EXAMPLE IV

Method of obtaining a mixture of the HYALASTINE and HYALECTIN fractions with no inflammatory activity:

Fresh or frozen cocks' combs, (3000 g) are minced in a meat mincer and then carefully homogenized in a mechanical homogenizer. The paste thus obtained is then treated in a stainless steel container AISI 316 or in a glass with 10 volumes of anhydrous acetone. The entire content is then agitated for 6 hours at a speed of 50 rpm and left to separate for 12 hours, after which the acetone is discarded by siphoning.

The acetone extraction is repeated until the discarded acetone reaches the right degree of humidity (Karl-Fischer method). The entire mixture is then centrifuged and vacuum dried at a suitable temperature for 5–8 hours. About 500–600 g of dry powder of cocks' combs are thus obtained.

300 g of dry powder are exposed to enzymatic digestion with papain (0.2 g) in aqueous conditions, buffered with phosphate buffer in the presence of a suitable quantity of hydrochloride cysteine. This mixture is agitated for 24 hours at 60 rpm, at a constant temperature of 60°–65° C. The mixture is then cooled at 25° C. and Celite$^R$ (60 g) is added, maintaining the agitation for another hour.

The mixture thus obtained is filtered until a clear liquid is obtained. The clear liquid then undergoes molecular ultrafiltration using membranes with a molecular exclusion limit of 30,000, in order to retain on the membrane those molecules with a molecular weight greater than 30,000. Five to six original volumes are ultrafiltered adding distilled water continually to the product in ultrafiltration. The added water is suspended and the ultrafiltration is continued until the volume is reduced to ⅓ of the original volume.

The residue liquid is rendered 0.1M by the addition of sodium chloride and the temperature is brought to 50° C. Under agitation at 60 rpm, 45 g of cetylpyridine chloride are added. This mixture is agitated for 60 minutes and then 50 g of Celite$^R$ are added. Under agitation, the temperature of the entire mixture is brought to 25° C. and the precipitate formed by centrifugation is gathered. The precipitate obtained is suspended in a 0.01M solution in sodium chloride (5 liters) containing 0.05% of cetylpyridinium chloride. It is agitated for 60 minutes at 50° C. The temperature is then brought to 25° C. and the precipitate is centrifuged.

The washing operation is repeated three times after which the precipitate is gathered in a container containing 3 liters of a solution at 0.05M of sodium chloride containing 0.05% of cetylpyridine chloride. Thus, it is agitated at 60 rpm for 60 minutes and the temperature is kept constant at 25° C. for two hours. The supernatant is eliminated by centrifugation.

The procedure is repeated several times with solutions of 0.1M sodium chloride containing 0.05% of cetylpyridinium chloride. The mixture is centrifuged and the supernatant is discarded. The precipitate is dispersed in a solution of 0.30M sodium chloride containing 0.05% of cetylpyridinium chloride (3 liters). The mixture is agitated and both the precipitate and the clear liquid are gathered. Extraction is repeated three more times on the precipitate, each time using 0.5 liter of the same aqueous solution.

Finally the precipitate residue is eliminated and the clear liquids are all placed together in a single container. The temperature of the liquid is brought to 50° C. while under constant agitation. The liquid is then brought to 0.23M with sodium chloride. 1 g of cetylpyridinium chloride is added, and it is kept under agitation for 12 hours. The mixture is cooled to 25° C. and then it is filtered first on Celite$^R$ pack and then through a filter. It then undergoes molecular ultrafiltration again, on a membrane with a molecular exclusion limit of 30,000 ultrafiltering three initial volumes with the addition of a solution of 0.33M sodium chloride. The addition of sodium chloride solution is interrupted and the volume is reduced to ¼ of the initial volume. The solution thus concentrated is precipitated under agitation (60 rpm) at 25° C. with 3 volumes of ethanol (95%).

The precipitate is gathered by centrifugation and the supernatant is discarded. The precipitate is dissolved in 1 liter of 0.1M solution in sodium chloride and the precipitation is repeated with 3 volumes of ethanol 95%. The precipitate is gathered and washed first with ethanol 75% three times, then with absolute ethanol (three times), and finally with absolute acetone (three times). The product thus obtained (HYALASTINE+HYALECTIN fractions) has an average molecular weight of between 250,000 and 350,000. The HY yield is equal to 0.6% of the original fresh tissue.

EXAMPLE V

Method of obtaining the HYALASTINE fraction from the mixture obtained by the method described in Example IV:

The mixture obtained by the method described in Example IV is dissolved in twice distilled apyrogenetic water at the rate of 10 mg of product to each 1 ml of water. The solution obtained is exposed to molecular filtration through filter membranes with a molecular exclusion limit of 200,000, following a concentration technique on the membrane without the addition of water. During the process of ultrafiltration through membranes with a molecular exclusion limit of 200,000, the molecules with a molecular weight of more than 200,000 do not pass through, while the smaller molecules pass through the membrane together with the water. During the filtration procedure no water is added, so that the volume decreases, and there is therefore an increase in the concentration of molecules with a molecular weight of more than 200,000. It is ultrafiltered until the volume on top of the membrane is reduced to 10% of the initial volume.

Two volumes of apyrogenetic twice distilled water are added and it is then ultrafiltered again until the volume is reduced to ⅓. The operation is repeated two more times.

The solution passed through the membrane is brought to 0.1M with sodium chloride and then precipitated with 4 volumes of ethanol at 95%. The precipitate is washed three times with ethanol at 75% and then vacuum dried. The product thus obtained (HYALASTINE fraction) has an average molecular weight of between 50,000 and 100,000. The HY yield is equal to 0.4% of the original fresh tissue.

EXAMPLE VI

Method of obtaining the HYALECTIN fraction:

The concentrated solution gathered in the container on top of the ultrafiltration membrane with a molecular exclusion of 200,000, as in example VI, is diluted with water until a solution containing 5 mg/ml of hyaluronic acid is obtained, as determined by quantitative analyses based on the dosage of glucuronic acid. The solution is brought to 0.1M in sodium chloride and then precipitated with 4 volumes of ethanol at 95%. The precipitate is washed three times with ethanol at 75% and then vacuum dried.

The product thus obtained (HYALECTIN fraction) has a molecular weight of between 500,000 and 730,000. This corresponds to a specific fraction of hyaluronic acid with a defined length of molecular chain of about 2,500 to 3,500 saccharidic units with a high degree of purity. The HY yield is equal to 0.2% of the original fresh tissue.

B. Evaluation of Biological and Pharmacological Activities of Molecular Weight Fractions of HA 1. Biological activity of cellular mobilization of the hyaluronic acid fractions:

The method, consisting of the determination of the detachment activity of fibroblasts in culture, was used as the method for evaluating the cell mobilization activity of the HA fractions.

Mouse BALB 3T3 cells were grown in Dulbecco's modified Eagle medium supplemented with 10% calf serum, penicillin (250 units/ml) and streptomycin (0.25 mg/ml), and were incubated in humidified 5% $CO_2$, 95% air at 37° C. For experimental purposes, cells were routinely inoculated in 60-mm diameter plastic tissue culture dishes ($6 \times 10^5$ cells/dish).

Confluent monolayers of 3T3 cells were decanted and fresh medium containing 2.0 mg/ml of different fractions of HA were added. At fixed intervals, the cell detachment was observed both microscopically and by counting the mobilized cells in a Coulter Counter.

Detachment Assay

To measure detachment kinetics, cells were inoculated into plastic dishes and allowed to grow for 24 hours. After this time, the culture medium was decanted and fresh medium containing 2.0 mg/ml of HA was added. Every 24 hours, two dishes, one each of test culture and of control culture, were decanted and both the cells in the supernatant and the attached cells were counted in a Coulter Counter.

Table 3 reports the results obtained with tests using the fractions obtained in the preparation Examples I-III above.

TABLE 3

| | RESULTS OF MOBILIZATION STUDIES | | |
|---|---|---|---|
| Fraction | Concentration (mg/ml) | No. of Detached Cells as Compared to Controls | % Effectiveness (as compared to control) |
| Control | | $2 \times 10^6$ | |
| HYALECTIN + HYALASTINE | 2 | $3.5 \times 10^6$ | 75 |
| HYALECTIN | 2 | $2.1 \times 10^6$ | 5 |
| HYALASTINE | 2 | $5 \times 10^6$ | 150 |

The data reported in Table 3 shows that the HYALASTINE fraction exhibits high cell mobilization activity making this fraction useful for wound healing applications. This cell mobilization activity of HYALASTINE will stimulate migration and proliferation of new cells when a pharmaceutical preparation of the fraction is applied to a damaged tissue area.

The HYALECTIN fraction, on the other hand, exhibits very little cell mobilization activity and would not, therefore, be useful for wound healing. HYALECTIN, however, because of its high average molecular weight and inherent viscosity, is useful for ocular and intraarticular injections, and the lack of appreciable cell mobilization activity is an important characteristic of the HYALECTIN fraction making it especially useful for intraocular and intraarticular injections.

2. Biological inflammatory activity of the hyaluronic acid fractions:

For this evaluation, the method of invasive cell count after intraocular administration in rabbits is utilized.

Method

Five (5) New Zealand or California rabbits, weighing about 2 kg and with ascertained perfect vision, are used for this test. The outer eye of the rabbits is checked for inflammatory processes at a macroscopic level and the inner eye is checked by ophthalmoscope. If the ocular fundus is clearly visible and normal, the test may proceed.

The selected animals undergo local anaesthetic by the installation of a few drops of a suitable sterile anaesthetic for ophthalmology; a few drops of atropine in ophthalmological solution are also instilled.

The test is carried out in sterile conditions. The ocular globe is made to protrude by means of pressure until it is possible to inject, through the sclera at about 5-6 mm from the limbus, at the center of the vitreal cavity, 100 μl of the solution, using a 26 G needle. The other eye is taken as a control. Two drops of antibiotic solution are instilled in the treated eye and the animals are then housed in single cages.

After 50-60 hours the test may proceed further. The eyes are checked in the same way as above for the selection of the animals. The animals are sacrificed with an intravenous injection of Pentothal. Then firstly, the aqueous humor (about 0.2 ml) is gathered by means of an insulin syringe with a 26 G needle. The ocular globes are then enucleated, freed from all foreign matter, washed in saline, dried with bibulous paper, and incised and opened in Petri plates, separating the main part of the vitreous humor and gathering it with a sterile syringe (about 0.7 ml). The vitreous humor is placed in small polyethylene test tubes and 50 μl of hyaluronidase (100 U NF/ml) is added. The mixture is then kept at a temperature of 37° C. for about 3 hours in order to render the solution less viscous.

A leukocyte count is carried out under a microscope by phase contrast (120 x) in a Burker chamber. A series of counts is effected on each sample, calculating the average values and expressing the result as the number of leukocytes per mm$^3$.

The test is considered positive when:
1. the eyes examined show no signs of suffering, and
2. the average number of leukocytes from at elast 4 of the 5 treated eyes does not exceed 200 per mm$^3$ and the average number of leukocytes from each control eye does not exceed 50 per mm$^3$.

Table 4 reports the results obtained from this evaluation using the HA fractions obtained in preparation Examples I-III discussed above.

TABLE 4

RESULTS OF INFLAMMATORY ACTIVITY STUDIES

| Fraction | No. of Invasive Cells |
|---|---|
| Control | 25 |
| HYALASTINE + HYALECTIN | 32 |
| HYALASTINE | 20 |
| HYALECTIN | 22 |
| Inflammatory Fraction (Avg. MW of <30,000) | 150 |
| Total Hyaluronic Acid from Rooster Combs (RF. Swann D. A. 1968, B.B.A. 156, 17-29) | 120 |

The results reported in Table 4 show that the HYALASTINE and HYALECTIN fractions exhibit no inflammatory activity above that for the control, and the combined HYALASTINE and HYALECTIN fraction showed only a negligible increase in inflammatory activity over the control. Accordingly, the HYALASTINE and HYALECTIN fractions are pharmaceutically useful with exhibiting undesirable inflammatory side effects. These results also further confirm the inventors discovery that it is the HA fraction having a low average molecular weight of less than about 30,000 which is responsible for the inflammatory activity of HA preparations. Hyaluronic acid from rooster combs, prepared according to the method described in the literature by Swarm (Swann D. A. 1968, B.B.A. 156, 17-29), shows a remarkable inflammatory activity.

It has thus been shown that the HYALASTINE fraction having an average molecular weight of about 50,000 to 100,000 exhibits high cell mobilization activity and is, therefore, useful in wound healing applications without exhibiting undesirable inflammatory reactions. The HYALECTIN fraction, having an average molecular weight of about 500,000 to 730,000, has been shown to be useful for ocular and intraarticular injection due to its high molecular weight and inherent viscosity, and, at the same time, does not stimulate cell mobilization activity or inflammatory reactions which are undesirable side effects to be avoided in these pharmaceutical applications.

More specifically, the HYALASTINE fraction has been found to be useful as a wound healing preparation because of the following characteristics.
1. The preparation promotes a remarkable shortened healing time, as compared to conventional therapy, with rapid clearing of the affected area, regularization of ulcer edges, vigorous development of granulation tissue, activation of cellular migration of macrophanges and fibroblasts and early epithelization.
2. The preparation promotes increased amenability to reconstructive surgery in the more severe cases.
3. The absence of keloid or retracting scar formation, with final reshaping of cicatricial tissue yielding good cosmetic and functional results.

The HYALASTINE preparation has been found to be useful for the treatment of various wounds including ducubitus sores (bed sores), trophic ulcers, burns, indolent wounds, post-traumatic ulcers, varicose and postphlebitic ulcers from venous blood stains, radionecroses, skin lesions, skin grafts and skin lesions due to herpes simplex. For these wound healing treatments, the HYALASTINE preparation, or the sodium salt thereof, can be administered in various methods, such as by gauze pads, cream, spray or ampoules for intradermal injection. For the topical applications as a cream or on a gauze pad, the HYALASTINE is preferably combined with an emulsifying agent, which absorbs the exudate from the exposed area while affording excellent diffusion of hyaluronic acid, and a water-dispersible excipient so that the wound dressing is easily removed.

The HYALECTIN fraction has been found to be particularly useful for the treatment of horses, particularly race horses, suffering from joint disorders and diseases caused by acute or chronic trauma, infections or repeated intraarticular corticosteroid injections. Specific examples of disorders treatable with HYALECTIN are osteoarthrosis with or without inflammatory signs, acute or chronic synoritis, degenerative pprocesses in articular cartilage, and dry joint flexion. The HYALECTIN fraction of the invention has been found to promote marked reduction of the healing time for such affected horses as compared with conventional therapy, to promote early and lasting improvement of joint function and to reduce pain and lameness. These clinically advantageous effects are believed to be promoted by a normalization of the viscoelasticity of the synovial fluid and by activation of tissue repair processes in the articular cartilages.

Moveover, all the above advantageous effects are promoted by the HYALECTIN fraction in the absence of local and/or systemic toxic effects. Reapeated administration of HYALECTIN produces no evidence of allergic reactions nor any adverse or lasting effects.

C. Pharmaceutical Preparations Comprising Molecular Weight Fractions of HA

The above disclosure has shown that the HYALASTINE and HYALECTIN fractions have good activity for pharmaceutical applications. The following examples are presented for exemplary purposes only to describe possible pharmaceutical preparations for actual in vivo administration of the HA fractions.

| 1. Preparations for Wound Healing: | | | |
|---|---|---|---|
| Example 1: | ampoules for intradermal injection - each ampoule contains: | | |
| | -Hyalastine sodium salt | mg | 4 |
| | -Sodium Chloride | mg | 16 |
| | -Water for injection q.s.a. | ml | 2 |
| Example 2: | ampoules for intradermal injection - each ampoule contains: | | |
| | -Hyalastine potassium salt | mg | 5 |
| | -Sodium Chloride | mg | 8 |
| | -Water for injection q.s.a. | ml | 1 |
| Example 3: | spray-bottle for topical application each bottle contains: | | |
| | -Hyalastine sodium salt | mg | 20 |
| | -Sodium Chloride | mg | 80 |
| | -Water for injection q.s.a. | ml | 10 |
| Example 4: | spray-bottle for topical application each bottle contains: | | |

|  |  |  |  |
|---|---|---|---|
|  | -Hyalastine potassium salt | mg | 30 |
|  | -Mannitol | mg | 100 |
|  | -Water for injection q.s.a. | ml | 10 |
| Example 5: | cream for topical application - each tube of cream contains: |  |  |
|  | -Hyalastine potassium salt | mg | 25 |
|  | -Polyethyleneglycol mono-stearate 400 | mg | 1000 |
|  | -Cetiol (decyl ester of oleic acid) | mg | 500 |
|  | -Lanette SX (cetyl-stearyl alcohol + lauryl sulfate 9:1) | mg | 150 |
|  | -Glycerol | mg | 200 |
|  | -Sorbitol | mg | 150 |
|  | -Na-dehydroacetate | mg | 10 |
|  | -p-oxymethylbenzoate | mg | 7.5 |
|  | -p-oxypropylbenzoate | mg | 5 |
|  | -redistilled water q.s.a. | g | 10 |
| Example 6: | cream for topical application - each tube of cream contains: |  |  |
|  | -Hyalastine sodium salt | mg | 30 |
|  | -Paraffin jelly | mg | 3 |
|  | -Polyethyleneglycol mono-stearate 400 | mg | 1000 |
|  | -Cetiol (decyl ester of oleic acid) | mg | 500 |
|  | -Lanette SX (cetyl-stearyl alcohol + lauryl sulfate 9:1) | mg | 150 |
|  | -Glycerol | mg | 200 |
|  | -Sorbitol | mg | 150 |
|  | -Na-dehydroacetate | mg | 10 |
|  | -p-oxymethylbenzoate | mg | 7.5 |
|  | -p-oxypropylbenzoate | mg | 5 |
|  | -redistilled water q.s.a. | g | 10 |
| Example 7: | medicated gauze pads for topical application - each gauze-pad measuring 10 × 10 cm contains: |  |  |
|  | -Hyalastine sodium salt | mg | 3 |
|  | -Glycerol | g | 1 |
|  | -Polyethyleneglycol | g | 2 |
|  | -redistilled water q.s.a. | g | 3 |
| Example 8: | medicated gauze-pads for topical application - each gauze-pad measuring 15 × 15 cm contains: |  |  |
|  | -Hyalastine potassium salt | mg | 6 |
|  | -Paraffin jelly | mg | 0.5 |
|  | -Glycerol | g | 1 |
|  | -Polyethyleneglycol | g | 2 |
|  | -redistilled water q.s.a. | g | 3 |
| Example 9: | dry powder for wound healing application - each gram of dry powder contains: |  |  |
|  | -Hyalastine sodium salt | mg | 10 |
|  | -Mannitol | g | 0.75 |
|  | -Glycine | g | 0.24 |
| 2. Preparations for Intraocular Use: |  |  |  |
| Example 10: | 1-ml vials - each vial contains: |  |  |
|  | -Hyalectin sodium salt | mg | 10 |
|  | -Sodium Chloride | mg | 8 |
|  | -Monobasic sodium phosphate 2H$_2$O | mg | 0.25 |
|  | -Dibasic sodium phosphate 12H$_2$O | mg | 3 |
|  | -Water for injection q.s.a. | ml | 1 |
| Example 11: | 5-ml vials - each vial contains: |  |  |
|  | -Hyalectin potassium salt | mg | 60 |
|  | -Mannitol | mg | 50 |
|  | -Monobasic sodium phosphate 2H$_2$O | mg | 1.25 |
|  | -Dibasic sodium phosphate 12H$_2$O | mg | 15 |
|  | -Water for injection q.s.a. | ml | 5 |
| Example 12: | preloaded syringes - each syringe contains: |  |  |
|  | -Hyalectin sodium salt | mg | 40 |
|  | -Sodium Chloride | mg | 16 |
|  | -Monobasic sodium phosphate 2H$_2$O | mg | 0.8 |
|  | -Dibasic sodium phosphate 12H$_2$0 | mg | 3.16 |
|  | -Water for injection q.s.a. | ml | 2 |
| 3. Preparations for Intra-Articular Use: |  |  |  |
| Example 13: | 2-ml vials each vial contains: |  |  |
|  | -Hyalectin sodium salt | mg | 40 |
|  | -Sodium Chloride | mg | 16 |
|  | -Water for injection q.s.a. | ml | 2 |
| Example 14: | 4-ml vials - each vial contains: |  |  |
|  | -Hyalectin potassium salt | mg | 60 |
|  | -Mannitol | mg | 35 |
|  | -Glycine | mg | 10 |
|  | -Water for injection q.s.a. | ml | 4 |
| Example 15: | preloaded syringes - each syringe contains: |  |  |
|  | -Hyalectin sodium salt | mg | 25 |
|  | -Sodium Chloride | mg | 12 |
|  | -Mannitol | mg | 10 |
|  | -Monobasic sodium phosphate 2H$_2$O | mg | 0.5 |
|  | -Dibasic sodium phosphate 12H$_2$O | mg | 6 |
|  | -Water for injection q.s.a. | ml | 2 |

Although the above-preparations have been described for exemplary purposes, it will be appreciated that other pharmaceutical formulations could be prepared by combining the HYALASTINE and HYALECTIN fractions discovered by the inventors, or the potassium or sodium salts thereof, with other pharmaceutically acceptable carriers, diluents, or excipients and at various doages depending upon the particular use for the formulation.

For wound healing uses, the preparations of the HYALASTINE fraction are applied to the affected skin areas in one of the dosage forms discussed above, that is, either as a cream, a spray, on a gauze-pad, as a dry powder or as an intradermal injection.

For lntraarticular uses, the preparations of the HYALECTIN are generally administered at a dosage rate of 2 ml per joint taken either from a prepared vial or a preloaded syringe as described above.

II. Use of Hyaluronic Acid and Molecular Weight Fractions thereof as a Vehicle for Drugs As discussed above, the present invention also relates to new medicaments or pharmaceutical compositions useful for topical and particularly ophthamological applications, the compositions comprising two components:

Component (1)—a pharmacologically active substance or an association or mixture of two or more active substances; and Component (2)—a vehicle of hyaluronic acid, a molecular fraction of the same or a salt thereof.

The application of a topically active medicament may be a benefit or remedy, and especially in dermatology, in diseases of the mucous membranes in general, and particularly diseases of the oral and nasal cavities, of the outer ear, and especially of the outer surface of the eye. These applications are particularly advisable in pediatrics and in the veterinary field.

The advantages of therapy using the medicaments according to the present invention are due to a more efficient vehicle for the drugs (i.e. Component (1)) promoted by the acidic polysaccharide of the Component (2) and to a better bioavailability at the active substance(s) compared to that obtainable with previous pharmaceutical formulations. Furthermore, the new medicaments of the invention assume particular importance in the case of ophthalmic medicaments, because in addition to the above mentioned qualities, there is a special compatibility with the corneal epithelium and, therefore, a very high level of tolerability with no sensitization effects. Furthermore, when the medicaments of the invention are administered in the form of concentrated solutions with elastic-viscose characteristics or in solid form, it is possible to obtain films on the corneal epithelium which are homogenous, stable, perfectly transparent, and which adhere well, guaranteeing prolonged bioavailability of the drug, and thereby forming excellent preparations with a retard effect.

Such ophthalmic medicaments are of exceptional value especially in the veterinary field, considering for example that there are at present no veterinary specialties for oculistic use, containing chemiotherapeutics. Indeed, preparations intended for human use are usually used, and these do not always guarantee a specific range of activity or they do not comply with the particular conditions in which the treatment should be effected. This is the case, for example, in therapy for infectious keratoconjunctivitis, pink eye or IBK, an infection which mainly affects cattle, sheep and goats. Presumably these three species have in common specific etiological factors. In particular: in cattle the main microorganism involved seems to be *Moraxella bovis* (even though other agents of a viral origin should not be excluded, such as Rhinotracheitis virus, in the case of sheep Micoplasma, Rickettsia and Chlamydia, and Rickettsia in the case of goats). The disease manifests itself in an acute form and tends to spread quickly: in the initial stages the symptomatology is characterized by blepharospasm and excessive lacrimation, followed by purulent exudate, conjunctivitis and keratitis, often accompanied by fever, reduced aperite and milk production. Lesions of the cornea are particularly serious and in the final stages can even cause perforations of the cornea itself. The clinical course varies from a few days to several weeks.

A vast range of chemiotherapeutic agents is used for treatment, administered both topically (often in association with antiinflammatory steroids), and systemically. Among these are the following: tetracyclines, such as oxytetracycline, penicillins, such as cloxacillin and benzylpenicillin, sulfamides, polymyxin B (associated with miconazole and prednisolone), chloramphenicol, tylosin and chloromycetin. Topical treatment of the disease, despite its apparent simplicity, still represents an unsolved problem, since for one reason or another it has proved impossible to obtain in the oculistic preparations used till now, concentrations of antibiotics or sulfamides which are therapeutically effective in the secretion of tears. This is quite understandable in the case of solutions, bearing in mind the mainly reclining position of the head in these animals, but it is also true of semi-solid medicaments, as the excipients normally used in them do not have the necessary qualities for adhering to the surface of the cornea, as they do not usually have a sufficiently high concentration of active substance and cannot achieve perfect distribution (i.e .., there is the presence of a distribution gradient). These defects of conventional colliriums in ophthalmic use have been described by Slatter et al. in "Austr. vet. J.," 1982, 59 (3), pp. 69–72.

One advantage of the present invention is the perfecting of new types of collirium in which these defects have been overcome. The presence of hyaluronic acid as a vehicle of the ophthalmic drugs allows for the formulation of excellent preparations free from concentration gradients of the active substance and, therefore, perfectly homogenous, transparent and adhesive to the corneal epithelium, without sensitization effects and with excellent vehicling of the active substance, possibly with a retard effect.

The above mentioned properties of the new medicaments may of course be used also in other fields besides ophthalmology. As already mentioned, they may be applied in dermatology and in diseases affecting the mucous membranes, such as in the mouth, for instance in odontology. They may also be used to obtain a systemic effect due to the effect of transcutaneous riabsorption, for instance in suppositories. All these applications are possible both in human and veterinary medicine. In human medicine the new medicaments are particularly suitable for use in pediatrics. The present invention therefore also includes in particular any one of the above therapeutic applications. For the sake of brevity, hereinafter, reference to the component (1) according to the invention is to be understood to also include the association or mixture of one or more active substances. In the present invention, therefore, hyaluronic acid or its molecular fractions are used as vehicles for the administration of pharmacologically active substances for topical use.

Thus, the present invention relates to new medicaments or pharmaceutical compositions useful in the above discussed therapeutic applications, the compositions comprising two components:

Component (1)—a pharmacologically active substance or an association or mixture of two or more pharmacologically active substances; and Component (2)—a vehicle of hyaluronic acid, a molecular weight fraction of the same, or a salt thereof.

A. Description of Components of Drug Vehicle System
Component (2):

Mixtures of hyaluronic acid with basic antibiotics have been described in literature and their negative effects have been discussed. For example in the article by Takashi et al., The Journal of Antibiotics, 150–155 (1978) some instances of interference between antibiotics and acidic polysaccharides in aqueous solutions are discussed.

But, medicaments for topical use with hyaluronic acid as a vehicle are new, and their use for pharmacological or preventive purposes is also new to the present invention.

As a vehicle to be used in the Component (2) of the present invention, hyaluronic acid of any origin may be used, such as the acids extracted from the above mentioned natural starting materials, such as cocks' combs. The preparation of crude extracts of such acids is described in literature. Preferably, purified hyaluronic acids should be used. According to the invention, in the place of integral hyaluronic acids obtained directly by extraction of the organic materials, it is possible to use fractions of the same with molecular weights which may vary greatly, such as for example from about 90–80% (MW=11.7–10.4 million) to 0.23% (MW=30,000) of the molecular weight of an integral acid having a molecular weight of 13 million, preferably between 5% and 0.23%. Such fractions may be obtained by various procedures such as by hydrolyzing, oxidizing or enzymatic chemical agents, physical procedures such as mechanical or by irradiation, and therefore, are often formed in the same purification procedures of the primary extracts (see for example the article by Balazs et al. in the above mentioned article in "Cosmetics and Toiletties"). The separation and purification of the fractions obtained is achieved for example by molecular filtration.

Of particular importance to be utilized as the vehicle (2) according to the present invention are two purified fractions discussed above which may be obtained from hyaluronic acid, for example the ones extracted from cocks'0 combs, and known as HYALASTINE and HYALECTIN. The fraction known as HYALASTINE has an average molecular weight of about 50,000 and 100,000, HYALECTIN has an average molecular weight of about 500,000 to 730,000. A combined fraction of these two fractions has also been isolated and characterized as having an average molecular weight of about 250,000 to about 350,000. This combined fractions may be obtained with a yield of 80% of total hyaluronic acid available from the particular starting material, while the fraction HYALECTIN may be obtained with a yield of 30% and the fraction HYALASTINE with a yield of 50% of the starting HY. The preparation of these fractions is described in Examples I-VI, hereinabove.

According to the invention, in place of hyaluronic acids and their molecular weight fractions as the component (2) of the medicaments, it is also possible to use their salts with inorganic bases, such as alkali metals (sodium, potassium, lithium), alkali earth metals (calcium, barium, strontium), magnesium, aluminum, ammonium or substituted ammonium (amines), for example mono, di, tri and tetra- alkylammonium where the alkyl groups have preferably beween 1 and 18 carbon atoms or arylalkyls with the same number of carbon atoms in the aliphatic portion and where aryl means a benzene residue, optionally substituted with between 1 and 3 methyl, halogen or hydroxy groups. These salts may be stoichiometrically neutral in the sense that all the acid functions are salified, or partial salts or acids, in which only a certain number of the acid functions are salified with the above mentioned metals. Such salts are easily obtained, for example, by reacting HY or the above mentioned fractions with the basic calculated quantity. It is also possible to use mixed salts originating from different bases. The ammonium salts of HY are formed by chemical reaction between hyaluronic acid and primary, secondary or tertiary amine moieties or ammonium hydroxide moieties of compounds or drugs having pharmaceutical activity.

That is, the present invention provides a means for utilizing HA as a carrier or delivery system for various drugs. The delivery system involves a combination of HA with basic drugs, whereby a complex is formed between HA and the drug. Formation of this complex can be represented by the following scheme:

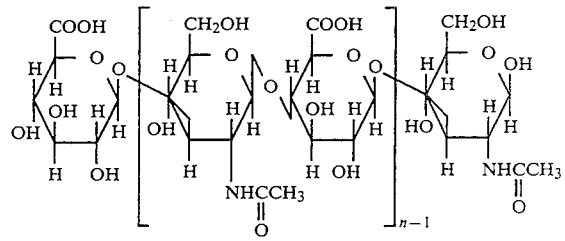

(hyaluronic acid comprised of repeating units of glucuronic acid and acetylglucosamine)

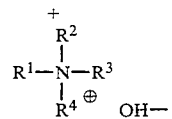

(drug having various structures but including basic portion)

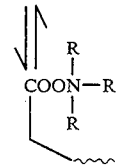

(Complex of HA and drug)

Thus the combination of HA plus a basic drug produces, according to the invention, a HA-drug complex as a delivery system for the drug. Drugs utilizable in the invention can be of various types, but are basic in nature existing as a 1°, 2°, 3° or 4° amine, whereby the basic amine portion of the drug will complex with the acidic portion of the HA molecule.

Component (1):

The component (1) described above may above all be catalogued, with respect to its use in the various fields of therapy, starting with the distinction between human and veterinary medicine and then specifying the various fields of application with respect to the organs or to the tissues to be treated, such as ophthalmology, dermatology, otorhinolaryngology, obstetrics, angiology, neurology or any type of pathology of the internal organs which may be topically treated, such as for example rectal applications. According to a particular aspect of the present invention, the pharmacological active substance component (1) is first and foremost for ophthalmic use. According to another criterion, the pharmacologically active substance (1) must be distinct with respect to its effect and may therefore, for example, be used as an anesthetic, analgesic, vasoconstrictor, antibacterial, antiviral, or anti-inflammatory agent. For the ophthalmic field, it may particularly be indicated for example for its: miotic, anti-inflammatory, wound healing and antimicrobial effects.

The component (1) may also be, according to the invention, an association or mixture of two or more active substances, as contained in many known medicaments. For example, in ophthalmology, an antibiotic may be associated with an antiphlogistic and a vasoconstritor, or several antibiotics may be associated with one or more antiphlogistics, or one or more antibiotics may be associated with a mydiatric or a miotic or wound healing or antiallergic agent, etc. For example it is possible to use the following associations of ophthalmic drugs: kanamycin+phenylephrine+phosphate d examethasone; kanamycin+phosphate betamethasone+phenylephrine, or similar associations with other antibiotics used in ophthalmology, such as rolitetracycline, neomycin, gentamicin and tetracycline.

In dermatology it is possible to use as the active component (1) associations of various antibiotics, such as erythromycin, gentamicin, neomycin, gramicidin, polymyxin B, mixtures of these antibiotics themselves, or mixtures of such antibiotics with anti-inflammatory agents, for example corticosteroids, for example hydrocortisone+neomycin; hydrocortisone+neomycin+polymyxin B+gralnicidin; dexamethasone+neomycin; fluorometholon+neomycin; prednisolone+neomycin; triamcinolone+neomycin+gramicidin+nistatine; or any other association used in conventional preparations for dermatology. The associations of various active substances are not of course limited to this field, but in each of the above mentioned fields of medicine it is possible to use associations similar to those already in use for the known pharmaceutical preparations of the art.

One particular form of medicament according to the invention is represented by mixtures of the pharmacologically active substance (1) with hyaluronic acids or their molecular fractions when the said substance (1) is of a basic nature, for example in the case of basic antibiotics. In this case, as discussed above, there is the formation between the acid HA component (2) and the drug substance (1) of stoichimetrically partial salts, or acid salts, in which an aliquot part of all the acid groups of the HA component (2) is salified with the basic groups of the drug component (1) or stoichiometrically neutral salts, in which all the groups of the HA component (2) are salified, or mixtures of these neutral salts with a further quantity of the basic active drug substance.

For the purpose of the present invention it is therefore possible to use in place of the mixtures of components (1) and (2), if a basic substance (1) is used, the above mentioned acid salts or those which are stoichiometrically neutral, or, of course mixtures of such salts both with component (1) and with component (2).

It is therefore possible, according to a particular aspect of the present invention, to use the above mentioned salts previously isolated and possibly purified, to the solid anhydrous state, as an amorphous powder, which when they come into contact with the tissue to be treated, constitute a concentrated aqueous solution of a gelatinous character, of a viscous consistency, and with elastic properties. These qualities are also maintained at stronger dilutions and may therefore be used in place of the above mentioned anhydrous salts, solutions in water at various degrees of concentration or in saline, possibly with the addition of other pharmaceutically acceptable excipients or additives, such as other mineral salts to regulate the pH and the osmotic pressure. It is also possible of course to use the salts to make gels, inserts, creams or ointments, in which there are other excipients or ingredients used in the traditional formulations of these pharmaceutical preparations. According to a particular aspect of the invention, there is a preference for the medicaments containing hyaluronic acid, the molecular weight fractions thereof or their mineral salts or their partial or neutral salts with the active substance (1) as the sole vehicle (with the possible exception of an aqueous solvent).

Hyaluronic acid or its molecular fractions may be substituted by their salts with inorganic bases, such as alkali metal (sodium, potassium, lithium), alkaline earth metal (calcium, barium, strontium), magnesium, aluminum, ammonium or substituted ammonium. This principal is also valid for the above mentioned partial acid salts, in which all the acid groups present may be partially or totally neutralized with the above mentioned metals, or with ammonia or with amines The ammonium salts are formed by chemical reaction between hyaluronic acid and primary, secondary or tertiary amine moieties or ammonium hydroxide moieties of compounds or drugs having pharmaceutical activity.

The hyaluronic acid to be utilized is a molecular weight fraction having a molecular weight broadly ranging from about 30,000 to about 13 million and preferably from about 30,000 to about 730,000. The most preferred hyaluronic fractions have a molecular weight of from about 50,000 to about 100,000, or from about 500,000 to about 730,000, or a combined fraction having a molecular weight of from 250,000 to about 350,000. These preferred fractions are importantly substantially free of low molecular weight hyaluronic acid having a molecular weight of less than about 30,000, and, therefore, are free of inflammatory side reactions when administered.

B. Summary of Drug Vehicle Systems According to the Invention

There are, therefore, various possibilities of realizing the medicaments according to the invention:

1. Physical mixtures—using a neutral or acidic active drug substance component (1) and mixing it or using it together with hyaluronic acid or its molecular fractions (referred together hereinafter as "hyaluronic acid") or their metallic salts. These mixtures may be represented as (using Na as an exemplary metal):
   a) acidic drug+HY
   b) acidic drug+HY—Na
   c) neutral drug+HY
   d) neutral drug+HY—Na 2. Complex of HY and drug—using partial salts of HY with a basic active drug substance component (1), leaving the residue acid groups of HY free or neutralizing them with the above mentioned metals or bases. These complexes may be represented as:

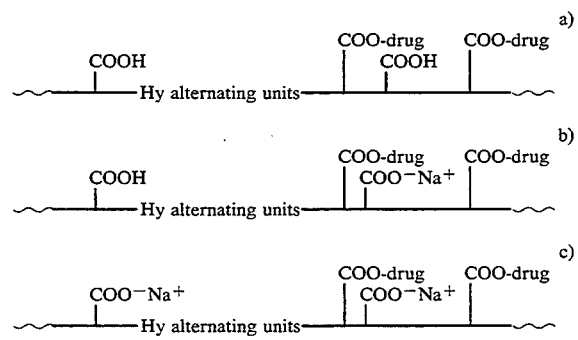

3. Complex of HY and drug—using stoichiometrically neutral salts of HY with a basic drug substance component (1), possibly adding HY or one of its partial or total metal salts (neutral). These may be represented as:

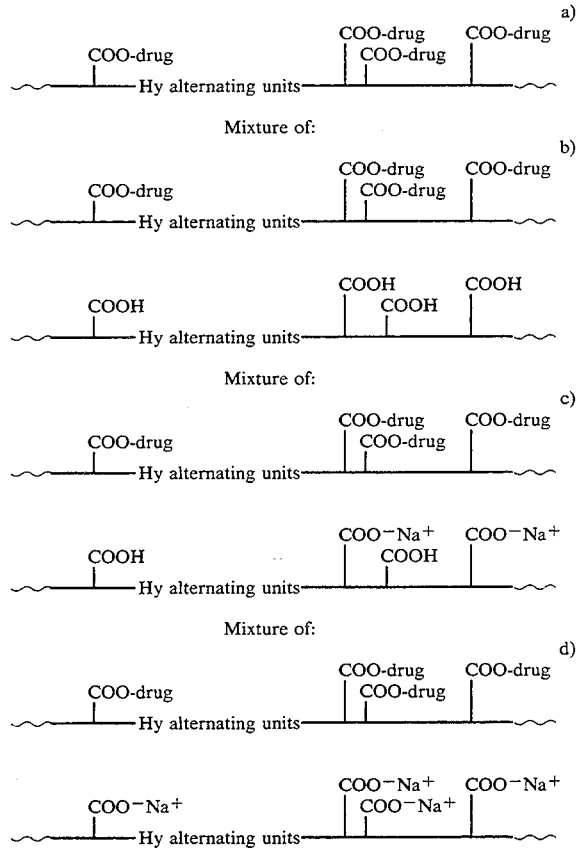

4. Complex of HY and drug—using stoichiometrically neutral salts of HY with a basic drug substance component (1), adding further quantities of the drug component (1).

5. Complex of HY and drug—using stoichiometrically neutral salts of HY with ad libitum mixtures of different drug components (1). These can be represented as:

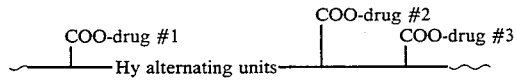

6. Mixtures of any of the above possible medicaments.

C. Specific Examples of Active Drug Component (1)

Examples of pharmacologically active substances (1) for use in opthalmic medicaments according to the invention are: basic and non basic antibiotics, or example aminoglucosidics, macrolides, tetracycline and peptides, such as for example gentamicin, neomycin, streptomycin, dihydrostreptomycin, kanamycin, amikacina, tobramycin, spectinomycin, erythromycin, oleandomycin, carbomycin, spiramycin, oxytetracycline, rolitetracycline, bacitracin, polymyxin B, gramicidin, colistin, chloramphenicol, lincomycin, vancomycin, novobiocin, ristocetin, clindamycin, amphotericin B, griseoofulvin, nystatin and possibly their salts, such as sulphates or nitrates, or associations between the same or with other active principles, such as those mentioned hereafter.

Other ophthalmic drugs to be used to advantage according to the present invention are: other anti-infective agents such as diethylcarbamazine, mebendazole, the sulfamides such as sulfacetamide, sulfadiazine, sulfisoxazole; antiviral and antitumoral agents such as iododeoxyuridine, adenine arabinoside, trifluorothtmidine, aciclovir, ethyldeoxyuridine, bromovinyldeoxyuridine, 5-iodo-5'-amino-2', 5'-dideoxyuridine; steroid anti-inflammatory agents, such as for example dexamethasone, hydrocortisone, prednisolone, fluorometholon, medrysone and possibly their esters, for example esters of phosphoric acid; non steroid anti-inflammatory agents, for example indomethacin, oxyphenbutazone, flurbiprofen; wound healers such as the epidermal growth factor EGF; local anesthetics, such as Benoxinate, proparacaine and possibly their salts; cholinergic agonist drugs such as pilocarpine, metacholine, carbamylcholine, aceclidine, physiostigmine, neostigmine, demecarium and possible their salts; cholinergic antagonist drugs such as atropine and its salts; the adrenergic agonisst drugs such as noradrenaline, adrenaline, naphazoline, methoxamine and possibly their salts; the adrenergic antagonist drugs such as propanolol, timolol, pindolol, bupranolol, atenolol, metoprolol, oxprenolol, practolol, butoxamine, sotalol, butadrine, labetalol and possibly their salts.

Associations or mixtures of such drugs between themselves and possibly with other principles may also be used as component (1) according to the invention. If in the place of only one active substance (1) association or mixtures of active substances are used, such as those mentioned above, the salts of the basic active substances and hyaluronic acid and its molecular fractions may be mixed salts of one or more of such basic substances or possibly mixed salts of this type with a certain number of other acid groups of the polysaccharide salified with the above mentioned metals or bases. For example it is possible to prepare salts of hyaluronic acid or one of the molecular fractions HYALASTINE or HYALECTIN with a certain percentage of salified acid groups with the antibiotic kanamycin, anothe percentage salified with the vasocostrictor phenylephrine, while maintaining a remaining percentage of free or salified acid groups, for example salified with sodium or another of the above mentioned metals. It is also possible to mix these type of mixed salts with other quantities of hyaluronic acid or its fractions or their metallic salts, as indicated above, for the medicaments containing salts of only one active substance with the aforesaid acidic polysaccharides.

Examples of active substances to be used alone or in combination or together with other active principles in dermatology are: therapeutic agents such as anti-infective, antibiotic, antimicrobial, anti-inflammatory, cytostatic, cytotoxic, antiviral, anesthetic agents, and prophylactic agents, such as sun shields, deodorants, antiseptics and disinfectants. Of the antibiotics the following are of particular note: erythromycin, bacitracin, gentamicin, neomycin, aureomycin, gramicidin and their associations; of the antibacterials and disinfectants: nitrofurazone, mafenids, chlorhexidine, and derivatives of 8-hydroxyquinoline and possibly their salts; of the anti-inflammatory agents: above all the cortocosteroids such as prednisolone, dexamethasone, flumethasone, clobetasol, triamcinolone acetonide, betamethasone or their esters, such as valerianares, benzoates, dipropionates; of the cytotoxics: fluorouracil, methotrexate, podophyllin; and of the anesthetics: dibucaine, lidocaine, and benzocaine. This list is of course only for illustrative purposes and any other agents known or described in literature may be used. Of the examples mentioned for ophthalmology and dermatology, it is possible to determine by analogy medicaments according to the present invention which are useful in the above mentioned fields of medicine, such as for example in otorhinolaryngology or odontology or in internal medicine, for example in endocrinology, where it is possible to effect treatments with preparations for intradermic absorption or absorption through the mucous, for example rectal or intranasal absorption, for example such as nasal sprays or inhalations in the oral cavity and in the pharynx. These preparations may, therefore, be for example anti-inflammatory, or vasoconstricting or vasopresors such as those already mentioned for ophthalmology, vitamins, antibiotics, such as those mentioned above, hormes, chemiotherapeutics, antibacterials, etc., these also as mentioned above for use in dermatology.

D. Method of Preparing HY Salts of the Invention

The preparation of the salts according to the invention may be carried out in a manner which is per se known, that is, by combining solutions or suspensions (in water or in organic solvents) of the two components (1) and (2) in calculated quantities and isolating the salts in an amorphous anhydrous form according to per se known techniques. It is also possible, in accordance with the previous discussions, to utilize bases or basic salts of components (1) and (2) with the above mentioned alkaline or alkaline earth metals or magnesium or aluminum or ammonium. It is possible, for example to (a) first prepare aqueous solutions of the two components (1) and (2), (b) freeze such components from aqueous solutions of their salts with acids of the respective metallic salts [for example sulphates in the case of component (1) and sodium salts in the case of component (2)]for treatment with ionic exchangers, and (c) unite the two solutions at a low temperature, for example between 0° and 20°. If the salt thus obtained is easily soluble in water, it should be freeze-dried, while salts which are not easily soluble may be separated by centrifugation, filtration or decantation and possibly then dessicated.

The invention is illustrated by the following examples:

EXAMPLE 1

Preparation of the Salt Hyaluronic Acid (HY) with Streptomycin 2.43 g of streptomycin sulfate (10 mEq) are solubilized in 25 ml of distilled $H_2O$. The solution is eluted in a thermostatic column at 5° C., containing 15 ml of quaternary ammonium resin (Dowex 1×8) in $OH^-$ form. The sulfate-free eluate is gathered in a thermostatic container at 5° C.

4.0 g of sodium salt of a hyaluronic acid with a molecular weight of 255,000 (corresponding to 10 mEq of a monomeric unit) are solubilized in 400 ml of distilled $H_2O$. The solution is then eluted in a thermostatic column at 5° C., containing 15 ml of sulfonic resin (Dowex 50×8) in $H^+$ form. The sodium-free eluate is gathered under agitation in the solution of streptomycin base. The resulting solution is frozen and instantly freeze-dried. In the salt thus obtained, all the acidic groups of hyaluronic acid are salified with the basic functions of streptomycin. Yield: 5.5 g.

Microbiological determination on *B. subtilis* ATCC 6633 compared to standard streptomycin showed a content of 33.8% in weight of streptomycin base, corresponding to the theoretically calculated weight. Colormetric determination of the glucuronic acid combined in polysaccharide according to the method of Bitter et al. (Anal. Biochem. 4, 330, 1962) shows a content in weight of HY acid of 66.2% (theoretical percentage—66.0%).

EXAMPLE 2

Preparation of the Salt of a Hyaluronic Acid (HY) with Erythromicine 4.0 g of sodium salt of a hyaluronic acid with a molecular weight of 77,000 (corresponding to 10 mEq of a monomeric unit) are solubilized in 400 ml of distilled $H_2O$. The solution is then eluted in a thermostatic column at 5° C., containing 15 ml of sulfonic resin (Dowex 50×8) in $H^+$ form. The eluate, free from sodium, is kept at a temperature of 5° C.

7.34 g of erythromycin base (10 mSq) are added to the solution of HY under agitation at 5° C. until complete solubilization is obtained. The resulting solution is frozen and freeze-dried. In the salt thus obtained all the acidic groups of hyaluronic acid are salified with erythromycin. Yield: 10.8 g.

Microbiological determination on *St. aureus* ATCC 6538 p in comparison with standard erythromycin shows a content of 66.0% in weight in erythromycin base, corresponding to the theoretical value. Colorimetric determination of the glucuronic acid combined in the polisaccharide according to the method of Bitter et al. (Anal. Biochem. 4, 330, 1962) shows a content of HY acid of 34.0%, corresponding to the theoretically calculated percentage.

EXAMPLE 3

Preparation of the Salt of a Hyaluronic Acid (HY) with Kanamycin 1.46 g of kanamycin sulphate (10 mEq) are solubilized in 25 ml of distilled $H_2O$. The solution is eluted in a thermostatic column at 5° C., containing 15 ml of quaternary ammonium resin (Dowex 1×8) $OH^-$ form. The eluate, free from sulfates is gathered ina thermostatic container at 5° C.

4.0 g of the sodium salt of HY with a molecular weight of 165,000 (corresponding to 10 mEq of a monomeric unit) are solubilized in 400 ml of distilled $H_2O$. The solution is then eluted in a thermostatic column at 5° C.

, containing 15 ml of sulfonic resin (Dowex 50 x 8) in $H^+$form. The eluate, free from sodium, is gathered under vortex agitation in the solution of kanamycin base. The solution thus obtained is instantly frozen and freeze-dried. Yield: 4.8 g. In the salt obtained all the acid groups of HY are salified with kanamycin.

Microbiological determination on *B. subtilis* ATCC 6633 in comparison with standard kanamycin shows a content of 24.2% in weight of kanamycin base, corresponding to the theoretically calculated percentage. Colormetric determination of the glucuronic acid combined in polysaccharide according to the method of Bitter et al. (Anal. Biochem. 4, 330, 1962) shows a content of HY acid of 75.8% in weight, also corresponding to the theoretical content.

EXAMPLE 4

Preparation of the Salt of a Hyaluronic Acid (HY) with Neomycin 1.52 g of neomycin sulfate (10 mEq) are solubilized in 20 ml of distilled H$_2$O and eluted in a thermostatic column at 5° C., containing 15 ml of quartenary ammonium resin (Dowex 1×8) OH$^-$form. The eluate, free from sulfates, is gathered in a thermostatic container at 5° C.

4.0 g of HY sodium salt with a molecular weight of 170,000 (corresponding to 10 mEq of a monomeric unit) are solubilized in 400 ml of distilled H$_2$O and eluted in a thermostatic column at 5° C. containing 15 ml of sulfonic resin (Dowex 50×8) in H$^+$form. The eluate, free from sodium is gathered under agitation in the solution of neomycin base. The viscoelastic precipitate which forms is separated by decantation and freeze-dried. Yield: 4.76 g. In the salt, all the HY acid groups are salified with neomycin.

Quantitative microbiological determination carried out on *St. aurens* ATCC 6538p compared to standard neomycin shows a content in weight of 21.2% of neomycin base, corresponding to the theoretically calculated value. Colorimetric determination of the glucuronic acid combined in polysaccharide according to the method of Bitter et al. (Anal. Biochem. 4, 330, 1962) shows an HY acid content of 78.8% in weight.

EXAMPLE 5

Preparation of the Salt of a Hyaluronic Acid (HY) with Gentamicin 1.45 g of gentamicin sulfate (10 mEq) are solubilized in 25 ml of distilled H$_2$O. The solution is eluted in a thermostatic column at 5° C., containing 15 ml of quaternary ammonium resin (Dowex 1×8) OH$^-$form. The eluate, free from sulfates, is gathered in a thermostatic container at 5° C.

4.0 g of sodium salt of HY with a molecular weight of 170,000 (corresponding to 10 mEq of a monomeric unit) are solubilized in 400 ml of distilled H$_2$O. The solution is then eluted in a thermostatic column at 5° C., containing 15 ml of sulfonic resin (Dowex 50×8) in H$^+$form. The eluate, free from sodium, is gathered under agitation in a vortex in the solution of gentamicin base. The thick and very viscous precipitate which forms is separated by decantation and freeze-dried. Yield: 4.65 g. In the salt thus obtained, all the HY acid groups are salified with gentamicin.

Quantitative microbiological determination carried out on *S. epidermidus* ATCC 12228 compared to standard gentamicin shows a content in weight of 20.0% of gentamicin base, corresponding to the theoretical content. Colorimetric determination of the glucuronic acid combined in polysaccharide according to the method of Bitter et al. (Anal. Biochem. 4, 330, 1962) shows an HY acid content of 80.0%.

EXAMPLE 6

Preparation of the Salt of a Hyaluronic Acid (HY) with Amikacin 1.47 g of amikacin base (10 mEq) are solubilized in 100 ml of distilled H$_2$O at 5° C.

4.0 g of sodium salt of HY with a molecular weight of 170,000 (corresponding to 10 mEq of a monomeric unit) are solubilized in 400 ml of distilled H$_2$O. The solution is then eluted in a thermostatic column at 5° C., containing 15 ml of sulfonic resin (Dowex 50×8) in H$^+$form.

The eluate, free from sodium, is gathered under agitation in a vortex in the solution of amikacin base. The thick and extremely viscous precipitate which forms is separated by decantation and freeze-dried. Yield: 5.16. g. In the salt thus obtained, all the HY acid groups are salified with amikacin.

Quantitative microbiological determination carried out on *St. aureus* ATCC 29737 in comparison to standard amikacina shows a content of 27.7% in weight in amikacina base, corresponding to the theoretical content. Colorimetric determination of the glucuronic acid combined in polysaccharide according to the method of Bitter et al. (Anal. Biochem. 4, 330, 1962) shows an HY acid content of 72.3% in weight.

EXAMPLE 7

Preparation of the Salt of a Hyaluronic Acid (HY) with Rolitetracycline 4.0 g of HY sodium salt with a molecular weight of 170,000 (corresponding to 10 mEq of a monomeric unit) are solubilized in 400 ml of distilled H$_2$O. The solution is then eluted in a thermostatic column at 5° C., containing 15 ml of sulfonic resin (Dowex 50×8) in H$^+$form. The eluate, free from sodium, is kept at a temperature of 5° C.

5.3 g of rolitetracycline base (10 mEq) are added to the solution of HY acid under agitation at 5° C. away from the light, until complete solubilization has been achieved. The solution thus Obtained is instantly frozen and freeze-dried. Yield: 8.9 g. In the salt thus obtained, all the HY acid groups are salified with rolitetracycline.

Microbiological determination on *B. pumilus* ATCC 14884 in comparison to standard rolitetracycline shows a content of 58.2% in weight of rolitetracycline base, corresponding to the theoretical value. Colorimetric determination of the glucuronic acid combined in polysaccharide according to the method of Bitter et al. (Anal. Biochem. 4, 330, 1962) shows an HY acid content of 41.8% in weight.

EXAMPLE 8

Preparation of the Salt of a Hyaluronic Acid (HY) with Polymyxin B 2.4 g of polymyxin B base (10 mEq) are suspended in 100 ml of distilled H$_2$O at 5° C.

4.0 g of HY sodium salt with a molecular weight of 170,000 (corresponding to 10 mEq of a monomeric unit) are solubilized in 400 ml of distilled H$_2$O. The solution is then eluted in a thermostatic column at 5° C., containing 15 ml of sulfonic resin (Dowex 50×8) in H$^+$form. The eluate, free from sodium, is gathered under vigorous agitation in the suspension of polymyxin base after 5° C. After an initial phase during which the solution becomes clear, there is a progressive formation of a not easily soluble product which is completely precipitated by 5 volumes of acetone. The precipitate is filtered, washed with acetone and then vacuum dried. Yield: 6.05 g. In the salt thus obtained, all the HY acid groups are salified with polymyxin B.

Quantitative microbiological determination carried out on *B. bronchiseptica* ATCC 4617 in comparison to standard polymyxin B shows a content of 38.7% in polymyxin B base, corresponding to the theoretical value. Colorimetric determination of the glucuronic acid combined in polysaccharide according to the method of Bitter et al. (Anal. Biochem. 4, 330, 1962) shows an HY acid content of 61.3%.

EXAMPLE 9

Preparation of the Salt of an (HY) Acid with Gramicidin S 6.7 g of hydrochloride gramicidin S (10 mEq) are suspended in 200 ml of ethanol/H$_2$O 80:20. The solution is then eluted in a thermostatic column at 5° C. containing 15 ml of quaternary ammonium resin (Dowex 1×8) in OH$^-$ form.

4.0 g of the sodium salt of HY with a molecular weight of 165,000 (corresponding to 10 mEq of a monomeric unit) are solubilized in 400 ml of distilled H$_2$O. The solution is then eluted in a thermostatic column at 5° C., containing 15 ml of sulfonic resin (Dowex 50×8) in H$^+$ form. 200 ml of DMSO are added to the eluate, free from sodiuum, and the mixture is kept under agitation at 5° C. The solution of gramicidin base is then slowly added. The resulting solution is precipitated by 10 volumes of acetone. The precipitate is filtered, washed with acetone and vacuum dried. Yield: 9.55 g. In the salt thus obtained, all the HY acid groups are salified with gramicidin S.

Quantitative microbiological determination carried out on *S. faecium* ATCC 10541 in comparison to standard gramicidin S shows a content of 60.0% of gramicidin S base, corresponding to the theoretical value. Colorimetric determination of the glucuronic acid combined in polysaccharide according to the method of Bitter et al. (Anal. Biochem.4, 330, 1962) shows an HY acid content of 40.0%.

EXAMPLE 10

Preparation of the Salt of a Hyaluronic Acid (HY) with Naphazoline

The pure naphazoline base was prepared as follows:
4.94 g of naphazoline—MCl (20 mM) are solubilized in 100 ml of distilled H$_2$O at 5° C. 20 ml of NH$_4$OH 5M are added and extracted twice with 100 ml of ethyl acetate. The organic layers are extracted twice with 50 ml of H$_2$O, mixed together again and anhydrified with anhydrous Na$_2$SO$_4$. The solution is concentrated at about 50 ml then placed in a freezer to crystalize. The crystalized product is filtered, washed with ethyl acetate and vacuum dried. Yield: 4.0 g of pure naphazoline base.

4.0 g of the HY sodium salt with a molecular weight of 625,000 (corresponding to 10 mEq of a monomeric unit) are solubilized in 400 ml of distilled H$_2$O and eluted in a thermostatic column at 5° C., containing 15 ml of sulfonic resin (Dowex 50×8) in H$^+$ form. The eluate, free from sodium, is kept at a temperature of 5° C. 2.1 g of the pure naphazoline base, (10 mSq) are added to the solution of HY acid and the mixture is agitated at 5° C. until complete solubilization is achieved. The resulting mixture is instantly frozen and freeze-dried. Yield: 5.72 g. In the salt thus obtained, all the HY acid groups are salified with naphazoline.

Quantitative spectrophotometric determination, carried out in comparison to naphazoline standard (USP) shows a content of 35.7% in weight in naphazoline base, corresponding to the theoretical value. Colorimetric determination of the glucuronic acid combined in polysaccharide according to the method of Bitter et al. (Anal. Biochem. 4, 330, 1962) shows an HY acid content of 64.3%.

EXAMPLE 11

Preparation of the Salt of a Hyaluronic Acid (HY) with Phenylephrine 2.04 g of L-phenylephrine-HCl (10 mEq) are solubilized in 25 ml of distilled H$_2$O. The solution is eluted in a thermostatic column at 5° C., containing 15 ml of quaternary ammonium resin (Dowex 1×8) in OH$^-$ form. The eluate, free from chlorides is gathered in a thermostatic container at 5° C.

4.0 g of the HY sodium salt with a molecular weight 820,000 (corresponding to 10 mEq of a monomeric unit) are solubilized in 400 ml of distilled H$_2$O. The solution is then eluted in a thermostatic column at 5° C., containing 15 ml of sulfonic resin (Dowex 50×8) in H$^+$ form. The eluate, free from sodium, is gathered under agitation in the solution of phenylephrine base. The resulting mixture is instantly frozen and freeze-dried. Yield: 5.25 g. In the salt thus obtained, all the HY acid groups are salified with phenylephrine.

U.V. spectrophotometric determination using the standard addition method (USP) shows a content of 30.6% in phenylephrine base, corresponding to the theoretical content. Colorimetric determination of the glucuronic acid combined in polysaccharide according to the method of Bitter et al. (Anal. Biochem. 4, 330, 1962) shows an HY acid content of 69.4%.

EXAMPLE 12

Preparation of the Salt of a Hyaluronic Acid (HY) with Atropine 4.0 g of the HY sodium salt with a molecular weight of 1,300,000 (corresponding to 10 mEq of a monomeric unit) are solubilized in 400 ml of distilled H$_2$O. The solution is then eluted in a thermostatic column at 5° C., containing 15 ml of sulfonic resin (Dowex 50×8) 0 in H$^+$ form. The eluate, free from sodium, is kept at a temperature of 5° C. 2.89 g of atropine base (10 mEq) are added to the solution of HY acid and the mixture is agitated at 5° C. The resulting mixture is frozen and freeze-dried. Yield: 6.5 g. In the salt thus obtained, all the hyaluronic acid groups are salified with atropine.

Quantitative gas chromotography determination (USP) carried out in comparison to standard atropine shows a content of 43.3% in atropine base, corresponding to the theoretical value. Colorimetric determination of the glucuronic acid combined in polysaccharide according to the method of Bitter et al. (Anal. Biochem. 4, 330, 1962) shows an HY acid content of 56.7%.

EXAMPLE 13

Preparation of the Salt of a Hyaluronic Acid (HY) with Pilocarpine 2.45 g of Pilocarpine-HCl (10 mEq) are solubilized in 50 ml di distilled H$_2$O. The solution is eluted in a thermostatic column at 5° C., containing 15 ml of quaternary ammonium resin (Dowex 1×8) in OH$^-$ form.

The eluate, free from chlorides is gathered in a thereostatic container at 5° C. 4.0 g of the HY sodium salt with a molecular weight of 170,000 (corresponding to 10 mEq of a monomeric unit) are solubilized in 400 ml of distilled H$_2$O. The solution is then eluted in a thermostatic column at 5° C., containing 15 ml of sulfonic resin (Dowex 50×8) in H$^+$ form. The eluate, free from sodium, is gathered under agitation in the solution of pilocarpine base. The solution thus obtained is instantly frozen and freeze-dried. Yield 5.25 g. In the salt thus obtained, all the HY acid groups are salified with Pilocarpine.

Spectrophotometric determination according to USP carried out in comparison to Pilocarpine standard shows a content of 35.1% in Pilocarpine base, corresponding to the theoretical value. Colorimetric determination of the glucuronic acid combined in polysaccharide according to the method of Bitter et al. (Anal. Biochem. 4, 330, 1962) shows an HY acid content of 64.6%.

EXAMPLE 14

Preparation of the Salt of a Hyaluronic Acid (HY) with Neomycin and with Polymixin 4.0 g of the HY sodium salt with a molecular weight of 170,000 (corresponding to 10 mEq of a monomeric unit) are solubilized in 400 ml of distilled $H_2O$. The solution is eluted in a thermostatic column at 5° C., containing 15 ml of sulfonic resin (Dowex 50×8) in $H^+$ form. The eluate, free from sodium is gathered in a thermostatic container at 5° C. 0.150 g of Polymyxin B base (0.63 mEq) are added under vigorous agitation. 1.425 g of Neomycin sulphate (9.37 mEq) are solubilized in 25 ml of distilled $H_2O$. The solution is eluted in a thermostatic column at 5° C., containing 15 ml of quaternary ammonium resin (Dowex 1×8) in $OH^-$ form.

The eluate, free from sulphates, is gathered under vigorous agitation in the solution of HY acid and Polymyxin B. The precipitate which forms is separated by centrifugation and vacuum dried; there is no loss of the product in the residual solution. Yield: 4.85 g.

17.25 mg of this product contain:
NEOMYCIN equal to 5.0 mg of NEOMYCIN SULPHATE
POLYMYXIN B equal to 0.63 mg (about 5000 UI) of POLYMYXIN SULPHATE N.B. Determinations were carried out after separation by HPLC of the two active principles.

EXAMPLE 15

Preparation of the Mixed Salt of Hyaluronic Acid (HY) with Kanamycin and with Phenylephrine 4.0 g of the HY sodium salt with a molecular weight of 65,000 (corresponding to 10 mEq of a monomeric unit) are solubilized in 400 ml of distilled $H_2O$. The solution is then eluted in a thermostatic column at 5° C., containing 15 ml of sulfonic resin (Dowex 50×8) in $H^+$ form.

The eluate, free from sodium, is gathered in a thermostatic container at 5° C. 0.85 g di kanamycin sulphate (5.82 mEq) are solubilized in 10 ml di distilled $H_2O$.

The solution is eluted in a thermostatic column at 520 C., containing 10 ml di quaternary ammoniim resin (Dowex 1×8) in $OH^-$ form.

The eluate, free from sulphates, is gathered in a container kept at a temperature of at 5° C.

The phenylephrine base is prepared by dissolving Phenylephrine-HCl in distilled $H_2O$ at 5° C. at 100 mg/ml, $NH_4OH$ 6N is added until complete precipitation is achieved. The precipitate is separated by filtration, washed with distilled $H_2O$ until the chlorides have disappeared from the washing water, and then vacuum dried.

The HY acid and kanamycin base solutions are mixed and kept at a temperature of 5° C., 699 mg of Phenylephrine base (4.18 mEq) are added under agitation until completely dissolved. The resulting solution is frozen and freeze-dried. Yield: 5.1 g.

Microbiological determination on *B. subtilis* ATCC 6633 in comparison to standard Kanamycin shows a content of 13.55% in Kanamycin base. U.V. spectrophotometric determination using the standard addition method (USP) shows a content of 13.45% in Phenylephrine base. Colorimetric determinatin of the glucuronic acid combined in polysaccharide according to the method of Bitter et al. (Anal. Biochem. 4, 330, 1962) shows a HY acid content of 73.0%.

EXAMPLE 16

Preparation of the Mixed Salt of a Hyaluronic Acid (HY) with Gentamicina, with Naphazoline and with Sodium 4.0 g of the HY sodium salt with a molecular weight of 50,000 (corresponding to 10 mEq of a monomeric unit) are solubilized in 400 ml of distilled $H_2O$. The solution is then eluted in a thermostatic column at 5° C., containing 15 ml of sulfonic resin (Dowex 50×8) in $H^+$ form.

The eluate, free from sodium is gathered in a thermostatic container at 5° C. 1.245 g of Gentamycin sulphate (8.59 mEq) are solubilized in 25 ml of distilled $H_2O$. The solution is eluted in a thermostatic column at 5° C., containing 12 ml of quarternary ammonium resin (Dowex 1×8) in $OH^-$ form. The eluate, free from sulphates, is gathered in a container kept at a temperature of 5° C.

The pure Naphazoline base is prepared with Naphazoline-HCl dissolved in distilled $H_2O$ at 5° C. at the concentration of 50 mg/ml, $NH_4OH$ 5M is added until pH12 and extracted twice with ethyl acetate.

The organic layers are washed with $H_2O$ and anhydrified on anhydrous $Na_2SO_4$. It is placed in a freezer to crystalize, the precipitate is filtered, washed with ethyl acetate and vacuum dried. 2.5 g of HY sodium salt and 0.297 g of Naphazoline base are added to the HY acid. (1.41 mEq) and agitated until completely solubilized. The solution of Gentamicina base is then added and homogenized and then frozen and freeze-dried. Yield: 7.35 g. Quantitative microbiological determination on *B. epidermidus* ATCC 12228 in comparison to Gentamicin standard shows a content of 11.1% of Gentamicin base. Quantitative spectrophotometric determination carried out in comparison to standard Naphazoline (USP) shows a content of 4.0% of Naphazoline base. Colorimetric determination of the glucuronic acid combined in polysaccharide according to the method of Bitter et al. (Anal. Biochem. 4, 330, 1962) shows a HY acid content of 83.0%.

EXAMPLE 17

Preparation of the Mixed Salt of a Hyaluronic Acid (HY) with Neomycin, with Phenylephrine and with Sodium 4.0 g of the HY sodium salt with a molecular weight of 65,000 (corresponding to 10 mEq of a monomeric unit) are solubilized in 400 ml of distilled $H_2O$. The solution is then eluted in a thermostatic column at 5° C., containing 15 ml of sulfonic resin (Dowex 50×8) in $H^+$ form. The eluate, free from sodium is gathered in a thermostatic container at 5° C.

1.28 g of Neomicin sulphate (8.42 mEq) are solubilized in 25 ml of distilled $H_2O$. The solution is eluted in a thermostatic column at 5° C., containing 12 ml of quaternary ammonium resin (Dowex 1×8) in OH⁻ form. The eluate, free from sulphates, is gathered in a Container kept at a temperature of 5° C.

The Phenylephrine base is prepared by dissolving Phenylephrine HCl in distilled H₂O at 5° C. at 100 mg/ml, NH₄OH 6N is added until complete precipitation is achieved. The precipitate is separated by filtration, washed with distilled H₂O until the chlorides have disappeared from the washing water, and then it is vacuum dried.

2.5 g of HY sodium salt and 2.266 g of Phenylephrine base (1.58 mEq) are added to a solution of HY acid and agitated until completely solubilized. The solution of Neomicin base is then added and after homogenization it is frozen and freeze-dried. Yield: 7.35 g.

U.V. spectrophotometric determination using the standard addition method (USP) shows a content of 3.57% in Phenylephrine base. Quantitative microbiological determination on *B. aureus* ATCC 6538p in comparison to Neomicina standard shows a content of 11.64% of Neomicina base. Colorimetric determination of the glucuronic acid combined in polysaccharide according to the method of Bitter et al. (Anal. Biochem. 4, 330, 1962) shows a HY acid content of 82.8%.

EXAMPLE 18

Preparation of the Salt of a Hyaluronic Acid (HY) with Pilocarpine and with Sodium 98.31 g of HY sodium salt with a molecular weight of 170,000 (corresponding to 245 mEq of a monomeric unit) are solubilized in 8.5 l of distilled H₂O.

The solution is then eluted in a thermostatic column at 5°, containing 300 ml of sulfonic resin (Dowex 50×8) in H⁺ form. The eluate, free from sodium, is gathered in a thermostatic container at 5° C.

2.35 g of Pilocarpine HCl (9.6 mEq) are solubilized in 50 ml of distilled H₂O. The solution is eluted in a thermostatic column at 5° C. containing 15 ml of quaternary ammonium resin (Dowex 1×8) in OH⁻ form.

The eluate, from from chlorides, is gathered under agitation in the solution of HY acid. 235.4 ml of a solution of sodium hydroxide 1M are slowly added under agitation. The solution thus obtained is instantly frozen and freeze-dried. Yield: 99.8 g. 100 mg of the product contain 2 mg of Pilocarpine as a base.

EXAMPLE 19

Preparation of the Salt of a Hyaluronic Acid (HY) with Streptomicina and with Sodium 98.68 g of HY sodium salt with a molecular weight of 255,000 (corresponding to 246 mEq of a monomeric unit) are solubilized in 8.5 l of distilled H₂O. The solution is then eluted in a thermostatic column at 5° C., containing 300 ml of sulfonic resin (Dowex 50×8) in H⁺ form. The eluate, free from sodium is gathered in a thermostatic container at 5° C.

1.88 g of Streptomicina sulphate (7.74 mEq) are solubilized in 20 ml of distilled H₂O. The solution is eluted in a thermostatic column at 5° C., containing 12 ml of quaternary ammonium resin (Dowex 1×8) in OH⁻ form. The eluate, free from sulphates, is gathered under agitation in the solution of HY acid. 238.3 ml of a solution of NaOH 1M are slowly added under agitation and the resulting solution is instantly frozen and freeze-dried. Yield: 99.8 g. 100 g of the product contain 1.5 g of Streptomicin as a base.

E. Biological Activity Studies

The present inventors have conducted an intensive investigation to study the capacity and efficiency of hyaluronic acid as a vehicle for various molecules and in particular ophthalmic drugs, guaranteeing perfect tolerability and compatibility (i.e., absence of sensitization phenomena) with the corneal epithelium.

To this end, a study was conducted to investigate the use of HA fractions having different molecular weights, particularly the HYALASTINE and HYALECTIN fractions, and a mixture of the same, for the preparation of different pharmaceutical forms, such as collyrium, gel, cream, inserts or dry powders. Therefore, ophthalmic drugs of different types were studied in order to obtain a broad understanding of the potential use of this biological polymer in its different fractions as a vehicle.

The experiments reported hereafter were aimed at studying formulations containing hyaluronic acid as an excipient are capable of enhancing the bioavailability of vehicled drugs or producing a synergistic effect in combination with the vehicled drugs, particularly with drugs having ophthalmic activity or utility.

These potential capacities of HA as a vehicle were investigated in the rabbit eye with four ophthalmic drugs of different types and actions, in particular, pilocarpine nitrate, triamcinolone, epidermal growth factor (EGF) and with the antibiotics streptomycin, erythromicin, neomycin and gentamicine. All of these drugs are known to have miotic, anti-inflammatory, healing and anti-microbial efficiency. Moreover evaluation of the activity of the antibiotic streptomycin, vehicled in hyaluronic acid, is very important because it is one of the most widely used antibiotics in ocular infections.

The studies reported hereinafter demonstrate the effects and superiority of utilizing the pharmaceutical compositions of the present invention comprising the drug component (1) together with the HY component (2) as compared to conventional administrations of the drug. Studies were Specifically designed to study the compositions of the invention wherein the drug component (1) and HY component (2) exist as a physical mixture and compositions wherein the drug component (1) exist as a salt complex with the HY component (2).

The experimental models studied and the experiments effected were as follows:

1) recovery activity from dry inflammation in the rabbit eye for hyaluronic acid salts of streptomycin, erythromycin, neomycin and gentamicin;

2) miotic activity of pilocarpine nitrate vehicled in hyaluronic acid in rabbit eye;

3) miotic activity of pilocarpine salified with hyaluronic acid in rabbit eye;

4) adhesive and filmogenous properties of pilocarpine salified with hyaluronic acid;

5) anti-inflammatory activity of triamcinolone vehicled in hyaluronic acid in the model of dextran-induced inflammation in rabbit eye;

6) healing activity of epidermal growth factor (EGF) vehicled in hyaluronic acid in a model of epithelial lesion of rabbit cornea.

7) antimicrobial activity of streptomycin vehicled in hyaluronic acid against *Bacillus subtilis* 6633 in agar plates;

8) antimicrobial activity of gentamicin vehicled in hyaluronic acid.

1) Recovery Activity From Dry Inflammation for Hyaluronic Acid Salts

Materials

Studies were carried out with hyaluronic acid salts of the antibiotics: streptomycin, erythromycin, neomycin and gentamicin. The salts utilized are the total salts in which all of the acid groups of hyaluronic acid are salified with a basic group of the antibiotic and prepared according to the procedures described hereinabove in Examples 1, 2, 4 and 5.

For administration, preparations were utilized comprising solutions of the HY drug complex in distilled water, having concentrations suitable to the antibiotic content:

hyaluronic acid + streptomycin (HYA1) 33.8%
hyaluronic acid + erythromycin (HYA2) 66.0%
hyaluronic acid + neomycin (HYA4) 21.2%
hyaluronic acid + gentamicin (HYA5) 20.0%

Method

The activity of the above HY salts was compared to that given by the same antibiotics dissolved in phosphate buffer and having the same concentrations of antibiotic. The activity of the two groups of products was measured on the basis of the time necessary to suppress a dry inflammation of the rabbit eye induced by a bacterial agent.

More precisely, the dry inflammation was determined in both eyes of 24 rabbits by intraocular injection of the titered suspension of one of the following bacterial groups: pseudomonas aeruginosa, staphylococcus aureus, salmonella typhi (0.1 ml). The various saline derivatives of the antibiotics were administered (3 drops every 6 hours) into the right eye (RE) of the rabbits, while into the left eye (LE) were instilled the corresponding quantities of the antibiotics dissolved in phosphate buffer. The treatment was begun immediately after injectin of the bacterial suspension and was continued until inflammation disappeared.

Both the eyes of each rabbit were observed with a slit lamp. In particular the following were examined: the state of the conjuntiva and the corneal epithelium, anterior chamber (presence of the Tyndall effect), the state of the iris of the posterior segment of the eye. The state of the back of the eye was examined with a Goldman lens. The presence of signs of inflammation (hyperemia, exudates, cloudiness of the liquids etc.) was registered. The percentage of eyes which did not present any signs of inflammation was then calculated.

The results are reported in Table 5. It can been seen from these results that administration of the HY-drug derivatives according to the present invention (HYA1-5) was followed by a more rapid recovery from inflammation compared to the administration of the corresponding antibiotics not salified with hyaluronic acid.

2) Miotic Activity of Pilocarpine Nitrate Vehicled in Hyaluronic Acid

Materials

The following materials were used as excipients for pilocarpine for the various pilocarpine nitrate formulations:

hyaluronic acid sodium salt, HYALASTINE fraction, (m.w., approximately 100,000), at a concentration of 10 mg/ml and 20 mg/ml;
hyaluronic acid sodium salt, HYALECTIN fraction (m.w. 500,000—730,000), at a concentration of 10 mg/ml and 20 mg/ml;
5% polyvinyl alcohol as a comparative ophthalmic excipient.

Various 2% formulations (collyrium or gel) of pilocarpine nitrate were prepared and vehicled by adding the two different fractions of HA sodium salt at a concentration of 10 and 20 mg/ml. The following solutions were prepared:

Formulation 1—saline with pilocarpine nitrate ($PiNO_3$) (2%), used as reference.

Formulation 2—solution of $PiNO_3$ (2%) vehicled in 5% polyvinyl alcohol, used as reference.

Formulation 3—solution of $PiNO_3$ (2%) vehicled in HYALASTINE fraction sodium salt (10 mg/ml).

Formulation 4—solution of $PiNO_3$ (2%) vehicled in HYALASTINE fraction sodium salt (20 mg/ml).

Formulation 5—solution of $PiNO_3$ (2%) vehicled in HYALECTIN fraction sodium salt (10 mg/ml).

TABLE 5

Effect of the administration of the derivatives HYA on recovery from dry inflammation in rabbit eye

| TREAT-MENT | DAYS FROM THE START OF INFLAMMATION | | | | | | | |
|---|---|---|---|---|---|---|---|---|
| | 1 | 2 | 3 | 4 | 5 | 6 | 7 | 8 |
| Streptomycin (6)* | 0.0 | 0.0 | 0.0 | 0.0 | 0.0 | 16.6 | 50.0 | 100.0 |
| HYA1 (6)* | 0.0 | 0.0 | 16.6 | 16.6 | 50.0 | 100.0 | 100.0 | 100.0 |
| Erthromycin (6)** | 0.0 | 0.0 | 0.0 | 0.0 | 0.0 | 0.0 | 16.6 | 33.3 |
| HYA2 (6)** | 0.0 | 0.0 | 0.0 | 0.0 | 16.6 | 16.6 | 33.3 | 50.0 |
| Neomycin (6)*** | 0.0 | 0.0 | 0.0 | 0.0 | 0.0 | 0.0 | 16.6 | 33.3 |
| HYA4 (6)*** | 0.0 | 0.0 | 0.0 | 16.6 | 16.6 | 33.3 | 33.3 | 50.0 |
| Gentamycin (6)* | 0.0 | 0.0 | 0.0 | 0.0 | 0.0 | 33.3 | 50.0 | 100.0 |
| HYA5 (6)* | 0.0 | 0.0 | 0.0 | 16.6 | 33.3 | 50.0 | 100.0 | 100.0 |

Values are expressed as percentages (number of eyes with inflammation out of the total number of eyes treated). Between brackets are the number of treated eyes.
*Injection of pseudomonas aeruginosa
**Injection of staphylococcus aureus
***Injection of salmonella typhi Formulation 6—solution of $PiNO_3$ (2%) vehicled in HYALECTIN fraction sodium salt (20 mg/ml).

Method

Albino New Zealand rabbits were used (2–2.5 kg). The formulation to be tested was instilled in one eye by microsyringe (10 1); the other eye served as a reference. The diameter of the pupil was measured in all cases at suitable time intervals. Each solution was tested on at least 8 rabbits. Each eye was treated not more than three times and a rest period of at least a week was observed between each treatment.

Parameters Measured

The pupil diameters were measured at various intervals in order to determine the miotic activity curve in time. The following activity parameters were subsequently calculated from the miosis/time graphs:

$I_{max}$ = maximum difference in pupil diameter between the treated eye and the reference.

Peak time = time taken to reach $I_{max}$.

Duration = time taken to restore basal conditions.

Plateau = period of absolute miotic activity.

AUC = area under miosis/time curve.

Results

The results of the tests are reported in Table 6. It can been seen from the data for the various parameters determined from the miotic activity time curve for all the solutions tested that the addition of hyaluronic acid to a 2% piiocarpine nitrate solution gives rise to an increase in miotic activity of the drug. In fact, the bioavailability of the drug may be as much as 2.7 times greater than that of the aqueous solution containing 2% pilocarpine nitrate (Formulation 1).

TABLE 6

Biological Activity of Ophthalmic Formulations Containing Pilocarpine-Nitrate Vehicled By Hyaluronic Acid[a]

| Formulation | Vehicle | $I_{max}$, mm (±LF 95%) | Peak time (minutes) | Duration (minutes) | Plateau (minutes) | AUC, cm$^2$ (±LF 95%) | Relative AUC |
|---|---|---|---|---|---|---|---|
| 1 | saline | 1.93 ± 0.35 | 20 | 110 | — | 117 ± 28 | 1 |
| 2 | 5% polyvinyl alcohol | 2.33 ± 0.28 | 20 | 140 | — | 192 ± 32 | 1.64 |
| 3 | hyalastine (10 mg/ml) | 2.50 ± 0.42 | 20 | 120 | — | 240 ± 40 | 2.05 |
| 4 | hyalastine (20 mg/ml) | 2.58 ± 0.38 | 30 | 150 | — | 208 ± 41 | 1.78 |
| 5 | hyalectin (10 mg/ml) | 2.50 ± 0.38 | 15 | 170 | — | 242 ± 48 | 2.06 |
| 6 | hyalectin (20 mg/ml) | 2.70 ± 0.38 | 20 | 190 | 45 | 320 ± 45 | 2.73 |

[a]Reported values represent a mean value for 8 runs.

It should also be noted that there is a statistically significant increase in activity when the HYALECTIN fraction of hyaluronic acid both at 10 and 20 mg/ml is used as a vehicle (Formulations 5-6), in contrast to the pilocarpine nitrate solution vehicled in polyvinyl alcohol (Formulation 2).

The use of hyaluronic acid as a vehicle is particularly interesting because the miotic activity of pilocarpine nitrate lasts longer when it is vehicled with this substance. That is, for the hyaluronic acid containing formulations the time taken to restore pupil diameter to basal conditions is up to 190 minutes (Formulation 6) as compared to 110 minutes for pilocarpine in saline along (Formulation 1).

3) Miotic Activity of Pilocarpine Salified With Hyaluronic Acid

Materials

For the various formulations of salified pilocarpine, the following products were used:

hyaluronic acid at low molecular weight (HYALASTINE fraction, m.w., approximately, 100,000) [HY$_1$];

hyaluronic acid sodium salt at high molecular weight (HYALECTIN fraction, m.w. between 500,000 and 730,000) [HA$_2$—Na] at concentrations of 10 mg/ml and 20 mg/ml;

polyvinyl alcohol 5% as ophthalmic vehicle to obtain comparison formulations.

The various formulations prepared were the following:

Formulation 1—saline with Pilocarpine nitrate (PiNO$_3$) 2% (used as a reference);

Formulation 2—solution of PiNO$_3$ 2% vehicled with polyvinyl alcohol 5% (used as a reference);

Formulation 3—solution of pilocarpine base/HY$_1$ acid in aqueous solution. The pilocarpine base content corresponds to 2%;

Formulation 4—solution containing pilocarpine salt/HA$_1$ acid vehicled with HY$_2$—Na 10 mg/ml. The pilocarpine base content corresponds to 2%;

Formulation 5—solution containing pilocarpine salt/HY$_1$ acid vehicled with HY$_2$—Na 20 mg/ml. The pilocarpine base content corresponds to 2%;

Formulation 6—inserts of HY$_2$—Na containing pilocarpine base salt with hyaluronic acid [HY$_1$]. The pilocarpine base corresponded to 6.25%.

Method

Albino New Zealand rabbits were used (2-2.5 kg). The solution to be tested was instilled in one eye of each of the rabbits with a microsyringe (10 ul); the other eye was used as a reference. The insert was placed in the conjunctival sac by means of suitable pincers. In all cases the pupil diameter was measured at suitable intervals. Each formulation was tested on at least 8 rabbits. Each eye was treated no more than three times; a rest period of at least a week was observed between each treatment.

Parameters

The pupil diameter was measured at various intervals of time in order to determine the miotic activity curve in time. The following activity parameters were subsequently calculated from the moisis/time graphs:

$I_{max}$=maximum difference in pupil diameter between the treated eye and the reference eye;

Peak time=time taken to reach the $I_{max}$;

duration=time taken to return to basal conditions;

plateau=period of absolute miotic activity;

AUC=area under the miosis/time curve.

Results

Table 7 reports the results of the tests where, for each solution tested, the values of the various parameters registered from the miotic activity in time curve are reported. It can be seen from the data that salification with hyaluronic acid of Pilocarpine at 2% causes an increase in miotic activity of the drug, whose activity can reach about 2 times that shown by an aqueous solution with pilocarpine nitrate 2% (Formulation 1).

A statistically significant increase in activity is also noted when hyaluronic acid with a high molecular weight is used as a vehicle both at 10 and 20 mg/ml (Formulations 4 and 5).

Salification with hyaluronic acid is particularly interesting also in relation to the longer duration of miotic activity of pilocarpine after vehicling with such formulations: The time taken to return to normal pupil diameter under basal conditions reaches values of 160 minutes (Formulation 3) compared to 110 minutes for pilocarpine (Formulation 1).

TABLE 7

Biological activity of the ophthalmic vehicles containing hyaluronic acid - Pilocarpine salified with hyaluronic acid

| Formulation No. | $I_{max}$, mm (±LF 95%) | Peak time min. | Duration min. | Plateau min. | AUC, cm$^2$ (±LF 95%) | relative AUC |
|---|---|---|---|---|---|---|
| 1 | 1.93 ± 0.35 | 20 | 110 | — | 117 ± 28 | 1.00 |
| 2 | 2.33 ± 0.28 | 20 | 140 | — | 192 ± 32 | 1.64 |
| 3 | 2.25 ± 0.28 | 20 | 160 | 20 | 212 ± 32 | 1.81 |
| 4 | 2.70 ± 0.43 | 30 | 180 | 40 | 280 ± 48 | 2.39 |
| 5 | 2.80 ± 0.20 | 15 | 200 | 45 | 361 ± 40 | 3.08 |

TABLE 7-continued

Biological activity of the ophthalmic vehicles containing hyaluronic acid - Pilocarpine salified with hyaluronic acid

| Formulation No. | $I_{max}$, mm (±LF 95%) | Peak time min. | Duration min. | Plateau min. | AUC, cm² (±LF 95%) | relative AUC |
|---|---|---|---|---|---|---|
| 6 | 3.70 ± 0.30 | 40 | 230 | — | 442 ± 70 | 3.78 |

4) Stability of the Corneal Films of the Hyaluronic Acid and Pilocarpine Derivatives The following experiments were designed to evaluate the adhesive and filmogenous properties of the derivatives of salification between pilocarpine and hyaluronic acid following application to the cornea of animals.

Materials

The following formulations are prepared (utilizing the hyaluronic acid products described above in Experiment 3):

Formulation 1—saline at 2% of pilocarpine nitrate ($PiNO_3$);

Formulation 2—solution at 2% of $PiNO_3$, thickened with polyvinyl alcohol 5% (Wacker Chemie, PVA W 48/20);

Formulation 3—solution containing pilocarpine base salt/$HY_1$ acid. The pilocarpine base content corresponds to 2%;

Formulation 4—solution containing pilocarpine base salt/$HY_1$ acid vehicled with $HY_2$—Na 10 mg/ml. The pilocarpine base content corresponds to 2%;

Formulation 5—solution containing pilocarpine base salt/$HY_1$ acid vehicled with $HY_2$—Na 20 mg/ml. The pilocarpine base content corresponds to 2%. All solutions contained 0.1% of sodium cluorescein.

The pH of the solutions was in all cases about 5.8.

Method

The test consisted in visually evaluating the formation, stability and duration of the film formed by the formulations on the cornea. To this end sodium fluorescein was added to the ophthalmic preparations (0.1%) and the eye was examined, after instillation in UV light of 366 nm.

12 albino rabbits were used in all (New Zealand, 2-2.5 kg) of both sexes. One drop (50 ul) of each vehicle was instilled in one eye of each rabbit, keeping the other eye as control.

Results

The parameters relative to the fluorescence: a) duration of the integral corneal film, b) duration of fluorescence (time necessary for the total disappearance of fluorescence from the eye), c) presence of fluorescence in the nose (time taken by the solution after application to appear at nose level), are reported in Table 8.

The derivatives of hyaluronic acid with pilocarpine produce a stable corneal film for periods of more than 2 hours. Transcorneal penetration of pilocarpine seems, therefore, to depend on the capacity of hyaluronic acid to vehicle the drug forming a homogenous and stable film on the cornea.

TABLE 8

| Formulation No. | Duration of integral film (min) | Duration of fluorescence (min) | Appearance of fluorescence in nose (min) |
|---|---|---|---|
| 1 | 30 | 100 | 2-3 |
| 2 | 80 | 150 | 10-15 |
| 3 | 100 | 150 | 5 |
| 4 | 120 | 180 | 15-20 |
| 5 | 140 | 210 | 50 |

5) Anti-Inflammatory Activity of Triamcinolone Vehicled In Hyaluronic Acid

Materials

The following were used:
solution of hyaluronic acid sodium salt-HYALECTIN fraction (m.w. between 500,000 and 730,000), 10 mg/ml in saline;
solution of triamcinolone (10% in saline).

Method

The experiments were carried out on male New Zealand rabbits (average weight 1.6 kg). After an adaption period of 5 days, introocular inflammation was induced in the rabbits by intraocular injection of dextran (10%, 0.1 ml). The administration was effected in both eyes under local anaesthetic with 4% Novesina, inserting the needle of the syringe at the edge of the cornea in the anterior chamber at a distance of 2 mm. The test was conducted on 10 animals.

Treatment

Treatment was effected in each animal both in the right and left eyes, by instillation of 3 drops 3 times a day for 6 days in all, of the following:

a solution of triamcinolone (10% in saline) in the left eye (LE);

a solution of hyaluronic acid sodium salt, HYALECTIN fraction, (10 mg/ml)+triamcinolone phosphate (10%) in the right eye (RE).

Parameters

The anti-inflammatory effect on the reaction induced by dextran was evaluated by observing the eye with a slit lamp at the following intervals: 0, 1 hr, 3 hr, 24 hr, 48 hr, 3 days, 4 days, 5 days and 6 days.

At the intervals, the eye examination evaluated the following observations:

the state of the cornea and conjunctiva for the possible presence of hypermia, edema, and especially observation of the iris which is normally sensitive to inflammatory processes after injection of inflammatory agents into the anterior chamber;

the Tyndall effect, in which the presence of opacity of varying intensity ("nubecula") is indicative of the presence of corpuscular (inflammatory) elements in the anterior chamber.

The result of the observation was expressed in terms of subjective scoring (from 0 to 3) related to the gradualness of the effect noted.

Results

It can be seen from the results as reported in Table 9 that administration of triamcinolone has an anti-inflammatory effect on the iris and causes the disappearance of opacity (Tyndall effect) in the anterior chamber. The inflammatory process which is evident from the 1st-3rd hour until the 3rd to 4th day progressively decreases until almost normal conditions are restored, with perfect limpidness of the eye by the 6th day. On the other hand, administration of hyaluronic acid sodium salt, HYALECTIN fraction, together with triamcinolone phosphate reduces intraocular inflammation observed at the times discussed above compared to administration of triamcinolone phosphate alone. That is, the inflammatory process in the iris and the opacity in the anterior chamber is seen to have decreased by the 24th hour, with progressive reduction at 48 hours and with total absence of inflammatory reaction from the 4th day on.

In the conjunctiva and the cornea, essentially no notable reactions were observed after intraocular injection of dextran.

Thus, the administration of triamcinolone phosphate together with the hyaluronic acid fraction resulted in 8 hours, 16 hours, 24 hours, 32 hours, 40 hours, and 48 hours.
Results Ophthalmological examination 1 as reported in Table 10, revealed that in the controls (Group 1) complete healing was achieved (5/5 animals) 48 hours after lesion. In the animals treated with EGF (Group 2) the healing process was apparent as early as 24 hours after scarification with considerable efficacy (4/5 animals).

TABLE 9

EFFECT OF THE COMBINATION OF HYALURONIC ACID AND TRIAMCINOLONE ON INTRAOCULAR INFLAMMATION INDUCED BY DEXTRAN

| | 0 | | 1 hour | | 3 hours | | 24 hours | | 48 hours | | 3 days | | 4 days | | 5 days | | 6 days | |
|---|---|---|---|---|---|---|---|---|---|---|---|---|---|---|---|---|---|---|
| | LE | RE | LE | RE | LE | RE | LE | RE | LE | RE | LE | RE | LE | RE | LE | RE | LE | RE |
| Conjunctiva | 0.0 | 0.0 | 0.2 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 |
| Cornea | 0.0 | 0.0 | 1.0 | 0.2 | 0.0 | 0.7 | 0.1 | 0.0 | 0.0 | 0.0 | 0.0 | 0.0 | 0.0 | 0.0 | 0.0 | 0.0 | 0.0 | 0.0 |
| Tyndall | 0.0 | 0.0 | 1.0 | 1.2 | 3.0 | 3.0 | 3.0 | 2.1 | 3.0 | 1.2 | 3.0 | 0.2 | 2.2 | 0.0 | 1.2 | 0.0 | 0.4 | 0.0 |
| Iris | 0.0 | 0.0 | 0.5 | 0.7 | 2.7 | 2.7 | 3.0 | 2.5 | 3.0 | 1.2 | 3.0 | 0.4 | 2.4 | 0.0 | 1.5 | 0.0 | 0.5 | 0.0 |

LE = Left eye, treated with triamcinolone.
RE = Right eye, treated with tiamcinolone and hyalectin.
[a]Each value is the mean of seven observations in a total of seven animals, and expressed in terms of subjective scoring between 0 and 3, in relation to the gradualness of the effect observed.

enhanced activity of the drug as evidenced by the more rapid recovery (faster decongestion) of the rabbit eye.

6) Healing Activity of EGF Vehicled in Hyaluronic Acid Materials.
Materials

The following were used:

Formulation A—EGF (Epidermal growth factor), dissolved in saline (0.5 mg/5 ml).

Formulation B—hyaluronic acid sodium salt, HYALASTINE fraction, (m.w. approximately 100,000) dissolved in saline (10 mg/ml).
Method The experiments were carried out on male albino New Zealand rabbits (average weight 1.8 kg). The animals, after a period of adaptation of about 5 days, underwent epithelial lesion of the cornea in suitable conditions of local anesthetic with Novesina (4%). The lesion consisted of a monocular scarification of a circular area in the optic zone effected by a concave glass cylinder ($\phi$ 3mm) with a sharp edge.
Treatment The animals were subdivided into groups, each group consisting of 5 animals, and subjected to pharmacological treatment by conjunctival instillation as follows:

| Group | Treatment |
|---|---|
| Group 1 (control) | Saline |
| Group 2 | EGF solution (Formulation A) |
| Group 3 | Solution of hyaluronic acid sodium salt, hyalastine fraction, + EGF solution - combination of Formulation A + Formulation B at 1:1 ratio to make Formulation C |

Treatment was effected on the right eye (RE) by conjunctival instillation of 2 drops every 8 hours for 3 total administrations.
Parameters Healing of the corneal epithelium was evaluated by observation of the eye and photographic documentation with a slit lamp at various intervals after scarification: 0, In the animals treated with the Formulation C comprising hyaluronic acid sodium salt, HYALASTINE fraction+EGF (Group 3) the healing process was complete in all the animals (5/5) as early as 16 hours after scarification.

These results show that utilization of the HYALASTINE hyaluronic acid fraction as a vehicle for EGF enhances the healing process by promoting more rapid effective healing of corneal lesions.

Antimicrobial Activity of Streptomycin Sulphate Vehicled in Hyaluronic Acid
Materials The following materials were used:

hyaluronic acid sodium salt, HYALASTINE fraction, (m.w. 100,000)

streptomycin sulphate standard (750 UI/mg) (2 mg/ml) in saline.

A solution of the two components (60 g hyaluronic acid sodium salt and 40 g streptomycin sulphate) was prepared and then freeze-dried.
Method The antimicrobial activity of the formulation of streptomycin in hyaluronic acid sodium salt, HYALASTINE fraction, was controlled by microbial assay by agar diffusion, based on the reading after a suitable period of incubation at 32° C., and on a comparison of the diameters of the microorganism's inhibition zones (*Bacillus subtillis* ATCC 6633) determined on the presumed concentrations of the antibiotic under examination and on the corresponding and known concentrations of the working standard.
Results After 18 hours of incubation of the assay plate at 32° C., it was observed that streptomycin vehicled in

TABLE 10

HEALING OF LESIONS IN THE CORNEAL EPITHELIUM

| | | Hours after scarification | | | | |
|---|---|---|---|---|---|---|
| Group | Treatment | 0 | 8 | 16 | 24 | 48 |
| 1 | Saline | + | + | + | + | − |
| | | + | + | + | + | − |
| | | + | + | + | + | − |
| | | + | + | + | + | − |
| | | + | + | + | + | − |

TABLE 10-continued

HEALING OF LESIONS IN THE CORNEAL EPITHELIUM

| Group | Treatment | 0 | 8 | 16 | 24 | 48 |
|---|---|---|---|---|---|---|
| 2 | EGF | + | + | + | − | − |
|   | (Formulation A) | + | + | + | − | − |
|   |   | + | + | + | + | − |
|   |   | + | + | + | − | − |
| 3 | Hyaluronic acid + | + | + | − | − | − |
|   | EGF (Formula- | + | + | − | − | − |
|   | tion C) | + | + | − | − | − |
|   |   | + | + | − | − | − |
|   |   | + | + | − | − | − |
|   |   | + | + | − | − | − |

Hours after scarification

+ = unhealed eye
− = healed eye hyaluronic acid maintains an antimicrobial activity which is equivalent to that of the streptomycin standard. The results (Table 11) were obtained by measuring the diameter of microbial inhibition zones at working concentrations of 20 and 5 UI/ml, and expressed in units of antimicrobial activity per miligram of the mixture compared to streptomycin sulphate.

TABLE 11

Antimicrobial Activity of Streptomycin Vehicled In Hyaluronic Acid, HYALASTINE Fraction, Compared To Streptomycin Sulphate Standard[a]

| Formulation | Theoretical (UI/MG) | Effective (UI/MG) |
|---|---|---|
| Streptomycin sulphate (1 mg) | 750 (1000 mg/gr) | 750 (control) (1000 mg/gr) |
| Streptomycin sulphate (0.40 mg) + Hyaluronic acid sodium salt - HYALASTINE fraction (0.60 mg) | 299 (400 mg/gr) | 295 (393 mg/gr) |

[a]The values reported in parenthesis are expressed as mg of streptomycin sulphate per mg of mixture.

8) Antimicrobial Activity of Gentamicine Vehicled in Hyaluronic Acid

Materials

The following materials were used:
Gentamicine dissolved in saline (50 mg/ml)
Hyaluronic acid sodium salt, HYALECTIN fraction (2 mg/ml)

Method

Septic phlogosis was caused in both eyes of 11 rabbits by intraocular injection of a titered suspension of *Pseudomonas aeruginosa* (0.1 ml). In those rabbits showing septic inflamation, hyaluronic acid, HYALECTIN fraction, in combination with gentamicine was administered by instillation in the right eye and gentamicine in a buffered saline vehicle was administered in the left eye. The treatment (3 drops every 6 hours) was begun immediately after injection of the infecting agent and was continued until the infection had disappeared. The rabbits' eyes were observed every day under a slit lamp.

Results

Treatment with a combination of gentamicine with hyaluronic acid resulted in a faster disappearance of the septic infection as compared to administration of the antibiotic alone. This conclusion is clear from the data presented in Table 12.

TABLE 12

EFFECT OF GENTAMICINE VEHICLED IN HYALURONIC ACID HYALECTIN FRACTION, ON INTRAOCULAR SEPTIC PHLOGOSIS

| Treatment | 1 | 2 | 3 | 4 | 5 | 6 | 7 |
|---|---|---|---|---|---|---|---|
| Gentamicine + Buffer Saline Vehicle | 0.0 | 0.0 | 0.0 | 0.0 | 0.0 | 36.3 | 100 |
| Gentamicine + Hyaluronic Acid HYALECTIN Fraction | 0.0 | 0.0 | 9.0+ | 27.2+ | 72.7+ | 100 | 100 |

Days from Start of Phlogosis

Values are expressed as percentages (number of eyes cured of phlogosis by the number of eyes treated).
+ = Significant difference vs buffer vehicle (less than 0.05, Fisher exact T-Test)

Additional examples, although not limitive, of ophthalmic drugs which can be vehicled with HA fractions according to the Invention are as follows:

| Antibiotics: | Chloramphenicol |
| | neomycin |
| | aureomycin |
| | myxin and polymyxin |
| | bacitracin |
| | mycetins |
| hormones: | nandrolone and nandrolone sulfate |
| anesthetics (local): | henoxinate and the hydrochloride thereof |
| antiviral: | iododeoxyuridine |
| | iododeoxycytidine |
| anti-inflammatories: | dexamethasone and the phosphate thereof |
| vasopressors and vasoconstrictors: | synephrine and neo-synephrine |

CONCLUSIONS

On the basis of the results obtained from the experiments discussed above, it can be concluded that solutions of hyaluronic acid sodium salt (in both the HYALASTINE and HYALECTIN fractions) can be used as a vehicle for ophthalmic drugs and proves to be efficient as such for various types of drugs having differing biological actions. For example, drugs including anti-glaucoma agents such as pilocarpine nitrate, anti-allergic and anti-inflammatory agents such as triamcinolone, tissue healing and cell proliferation promoting agents for promoting healing of eye tissue such as EGF, and antibiotics such as streptomycin and gentamicine, whose miotic, anti-inflammatory, healing and antimicrobial activities respectively are reported, can all be administered effectively utilizing HA as a vehicle.

The formulations of ophthalmic drugs vehicled in hyaluronic acid fractions with various molecular weights prove to be perfectly tolerated by the host, and compatible with the corneal epithelium without, therefore, giving rise to sensitization phenomena.

It is also possible from the data to observe how this biological product, hyaluronic acid, is an efficient vehicle, capable of enhancing the in vivo bioavailability of vehicled drugs, strengthening the pharmacological activity of such drugs. The use of hyaluronic acid fractions as a drug vehicle particularly results in:

an increase in the miotic activity of pilocarpine nitrate while prolonging the activity time of the drug;

an increase in the anti-inflammatory activity or triamcinolone on intraocular inflammation induced by dextran, with a regression of the phlogistic process in shorter times as compared to those obtained with triamcinolone alone;

an increase in the protective action of epidermal growth factor (EGF) on superficial lesions in the cornea with obvious synergism and reduction in healing times as compared to recovery times with EGF alone; and an increase in the in vivo biological activity of antibiotics, such as gentamicine.

The results obtained by using this biological polymer, hyaluronic acid, as a vehicle for drugs with such varied natures and actions, allows for the extrapolation of its potential as a vehicle for numerous other ophthalmic drugs.

In addition, the results reported above show that hyaluronic acid and its molecular weight fraction, particularly the HYALASTINE and HYALECTIN fraction, are useful drug vehicles when used in physical admixture with a drug or when used in salt complex with a basic drug.

F. Pharmaceutical Preparations Utilizing HY as a Drug Vehicle

As discussed above, the medicaments according to the present invention utilize HY as a vehicle for pharmacologically active drugs by the use of medicaments containing an active drug component (1) together with a HY component (2), either as a physical mixture or as a complex of the acidic HY with a basic drug. In preparing these medicaments according to the invention, the quantitative ratios in weight of the two components (1),and (2) may vary within ample limits. The particular ratio, naturally, depends also on the nature of the two components, and particularly on that of the active drug substance. For example, the weight ratios of the two components (1) and (2) may range between 0.01:1 and 100:1. The range of variation, however, is preferably between the limits of 0.01:1 and 10:1 for the two said components and especially between 0.1:1 and 2:1.

The medicaments according to the invention may be in solid form, for example freeze-dried powders containing only the two components in mixture or separately packed. In solid form, such medicaments form, on contact with the epithelium to be treated, more or less concentrated solutions according to the nature of the particular epithelium with the same characteristics of the previously prepared solutions in vitro which represent another particularly important aspect of the present invention. Such solutions are preferably in distilled water or sterile saline and preferably contain no other pharmaceutical vehicle besides hyaluronic acid or one of its salts. The concentrations of such solutions may also vary within ample limits, for example between 0.01 and 75% for each of the two components taken separately, and for their mixtures or salts. There is a particular preferance for solutions of a pronounced elastic-viscose character, for example with a content of between 10% and 90% of the medicament or of each of its components.

Medicaments of this type are particularly important for ophthalmic use, both in an anhydrous form (freeze-dried powders), concentrated solutions or diluted in water or saline, possibly with the combination of additive or auxilary substances, such as in particular disinfectant substances or mineral salts acting as a buffer or other purposes.

Among the medicaments of the invention the following are particularly important, while considering for each case the degree of acidity suiting the place to which the medicament is to be applied, that is, with a physiologically tolerable pH. Adjustment of the pH, for example in the above mentioned salts of hyaluronic acid with a basic active substance, may be effected by regulating in a suitable manner the quantities of the polysaccharide, of its salts and of the basic substance itself. Thus, for example, should the acidity of a hyaluronic acid salt with a basic substance be too high, the excess of the free acid groups with the above mentioned inorganic bases can be neutralized, for example with sodium or potassium or ammonium hydrate.

Reported below are various examples of different formulations according to the invention containing hyaluronic acid, particularly ophthalmic drugs, which may be in the form of powders, collyrium, gel, cream, or inserts, in which hyaluronic acid in its different fractions, HYALASTINE and HYALECTIN, is the excipient used:

| | | |
|---|---|---|
| Example 20 | - A gel containing EGF of which 100 g contain: | |
| | - HY sodium salt HYALASTINE fraction | 55 g |
| | - HY sodium salt HYALECTIN fraction | 30 g |
| | - EGF | 0.5 g |
| | - twice distilled water | 23.5 g |
| Example 21 | - A 100 mg insert with pilocarpine nitrate containing: | |
| | - HY sodium salt HYALASTINE fraction | 100 g |
| | - pilocarpine nitrate | 2 g |
| Example 22 | A powder form for topical application containing streptomycin. 100 gr of powder contain: | |
| | - HY sodium salt HYALASTINE fraction | 70 g |
| | -HY sodium salt HYALECTIN fraction | 28.5 g |
| | -streptomycin | 1.5 g |
| Example 23 | - A 100 mg insert with pilocarpine containing: | |
| | - mixed salt of hyaluronic acid with pilocarpine and with sodium (see preparation in example 18) | 100 g |
| Example 24 | - A collirium containing gentamicin and napazoline, of which 100 ml contain: | |
| | - mixed salt of hyaluronic acid with gentamicin, with naphazoline and with sodium (see preparation in example 16) | 2.910 g |
| | - propyl oxybenzoate | 0.050 g |
| | - sodium phosphate | 1.500 g |
| | - distilled water q.b.a. | 100 ml |
| Example 25 | - A collirium with chloramphenicol, neomycin, phenylephrine, nitrofurazone, of which 100 ml contain: | |
| | - mixed salt of hyaluronic acid with neomycin, with phenylephrine and with sodium (see preparation example 17) | 2.390 g |
| | - chloramphenicol | 0.500 g |
| | - nitrofurazone | 0.02 g |
| | - distilled water q.b.a. | 100 ml |
| Example 26 | - A collirium with dexametasone phosphate, kanamycin E phenylephrine, of which 100 ml contain: | |
| | - mixed salt of hyaluronic acid with kanamycin and phenylephrine (see preparation Example 15) | 3.060 g |
| | - dexametasone phosphate sodium salt | 0.100 g |
| | - methyl p-hydroxybenzoate | 0.060 g |
| | - distilled water q.b.a. | 100 ml |
| Example 27 | - a collyrium which may be used as "artificial tears", containing: | |
| | - a hyaluronic acid sodium salt HYALECTIN fraction | 10 mg |
| | - saline buffered with phosphate pH 7.6 M | 10 ml |

| | |
|---|---|
| Example 28 | - a collyrium which may be used as "artificial tears", containing: |
| | - hyaluronic acid sodium salt HYALECTIN fraction    20 mg |
| | - saline buffered with phosphate pH 7.6 M    10 mg |

Although the above preparations have been described for exemplary purposes, it will be appreciated that the pharmaceutical formulations could be prepared by combining the hyaluronic fractions, particularly, the HYALECTIN or HYALASTINE fractions or the combined hyalectin/hyalastine fraction, or the potassium or sodium salts thereof, with other active drugs, and at various dosages depending upon the particular use for the formulation.

Hyaluronic acid, particularly in the substantially pure HYALECTIN and HYALASTINE fractions, has therefore, been shown to be an effective vehicle or excipient for use in combination with various drugs having ophthalmic utility or activity. Pharmaceutical compositions containing the HA fractions as the drug vehicle are particularly useful because the HA fractions exhibit a high level of tolerability to the eye and a high compatibility with the corneal epithelium. Use of the HA fractions, moreover, provides a means for actually enhancing the in vivo biological activity of ophthalmic drugs. The use of the particular HYALECTIN and HYALASTINE HA fractions is further useful and important because these fractions, when administered in the eye, do not exhibit undesirable inflammatory side reactions.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

We claim:

1. A partial or a stoichiometrically neutral salt of hyaluronic acid or a molecular weight fraction thereof with at least one pharmacologically active substance of a basic nature suitable for topical administration.

2. A salt of hyaluronic acid according to claim 1, wherein said salt is a partial salt wherein a first portion of the acid groups of the hyaluronic acid is salified with at least one pharmacologically active substance suitable for topical administration.

3. A salt of hyaluronic acid according to claim 2, wherein a second portion of the acid groups of said hyaluronic acid is salified with an alkali or an alkaline earth metal, magnesium, aluminum or ammonium.

4. A salt of hyaluronic acid according to claim 2, wherein a second portion of the acid groups of said hyaluronic acid is salified with an alkali or an alkaline earth metal, magnesium, aluminum or ammonium.

5. A salt of hyaluronic acid according to claim 1, wherein said hyaluronic acid is a fraction having an average molecular weight between about 30,000 and 730,000.

6. A salt of hyaluronic acid according to claim 5, wherein said fraction is substantially free of hyaluronic acid having a molecular weight less than 30,000.

7. A salt of hyaluronic acid according to claim 6, wherein said fraction has an average molecular weight between about 50,000 and 100,000.

8. A salt of hyaluronic acid according to claim 6, wherein said fraction has an average molecular weight between about 500,000 and 730,000.

9. A salt of hyaluronic acid according to any one of claims 1, 4, 6 and 7, wherein said active substance is suitable for ophthalmological use.

10. A salt of hyaluronic acid according to claim 1, wherein said active substance is suitable for dermatological, otorhinolaryngological odontological, angiological, obstetrical or neurological use.

11. A salt of hyaluronic acid according to any one of claims 1, 4, 6 and 7, wherein said pharmacologically active substance is an antibiotic, anti-infective, antiviral, antimicrobial, antiinflammatory, wound healing, cytostatic, cytotoxic, anesthetic, cholinergic promotor, cholinergic antagonist, adrenergic promotor or adrenergic antagonist agent.

12. A salt of hyaluronic acid according to claim 1, wherein said pharmacologically active substance is a member selected from the group consisting of erythromycin, gentamycin, neomycin, streptomycin, dihydrostreptomycin, kanamycin, amikacyn, tobramycin, spectinomycin, erythromycin, oleandomycin, carbomycin, spiramycin, oxytetracycline, rolitetracycline, bacitracin, polymyxin B, gramicidin, colistin, chloramphenicol, lincomycin, vancomycin, novobiocin, ristocetine, clindamycin, amphotericin B, griseofulvin, nystatin, diethylcarbamazine, mebendazol, sulfacetamide, sulfadiazine, sulfisoxazole, iodeoxuridine, adenine arabinoside, trifluorothimidine, aciclovir, ethyldeoxyuridine, pilocarpine, metacholine, carbamylcholine, aceclidine, fisostigmine, neostigmine, demecarium, atropina, noradrenalin, adrenalin, norfazoline, methoxamine, propanolol timolol, pindolol, bupranolol, atenolol, metoprolol, oxyprenolol, practolol, butoxamine, sotalol, butadrine and labetalol.

13. A salt of hyaluronic acid according to any one of claims 1, 4, 6 and 7 wherein said active substance is a member selected from the group consisting of streptomycin, erefthromycin, kanamycin, neomycin, gentamicin, pilocarpine, triamcinolone and epidermal growth factor.

14. A pharmaceutical composition which comprises as an active ingredient a pharmacologically effective amount of a partial or a stoichiometrically neutral salt of hyaluronic acid or a molecular weight fraction thereof with at least one pharmacologically active substance of a basic nature suitable for topical administration, with the proviso that said active substance is not capable of being absorbed intradermally or through the nasal or rectal mucosa.

15. A pharmaceutical composition according to claim 14, wherein said salt is a partial salt wherein a first portion of the acid groups of the hyaluronic acid is salified with at least one pharmacologically active substance suitable for topical administration.

16. A pharmaceutical composition according to claim 15, wherein a second portion of the acid groups of said hyaluronic acid is salified with an alkali or an alkaline earth metal, magnesium, aluminum or ammonium.

17. A pharmaceutical composition according to claim 14, wherein said salt is a stoichiometrically neutral salt in which all of the acid groups of the hyaluronic acid are salified with a pharmacologically active substance suitable for topical administration, an alkali or alkaline earth metal, magnesium, aluminum or ammonium.

18. A pharmaceutical composition according to claim 14, wherein said hyaluronic acid is a fraction having an average molecular weight between about 30,000 and 730,000.

19. A pharmaceutical composition according to claim 18, wherein said fraction is substantially free of hyaluronic acid having a molecular weight less than 30,000.

20. A pharmaceutical composition according to claim 19, wherein said fraction has an average molecular weight between about 50,000 and 100,000, or between about 500,000 and 730,000.

21. A pharmaceutical composition comprising as an active ingredient a salt of hyaluronic acid according to claim 12, together with an excipient suitable for topical administration.

22. A pharmaceutical composition comprising as an active ingredient a salt of hyaluronic acid according to claim 13, together with an excipient suitable for topical administration.

23. A method for treating ophthalmic conditions, dermatological conditions, diseases of the mucous of the oral and nasal cavities or diseases of the outer ear, comprising administering a salt of hyaluronic acid according to claim 1 or 14.

24. A method for treating ophthalmic conditions comprising administering a salt of hyaluronic acid according to claim 11 or 14.

25. A pharmaceutical composition according to claim 12, wherein said hyaluronic acid is a fraction having an average molecular weight between about 30,000 and 730,000.

26. A pharmaceutical composition according to claim 25, wherein said fraction is substantially free of hyaluronic acid having a molecular weight less than 30,000.

27. A pharmaceutical composition according to claim 26, wherein said fraction has an average molecular weight between about 50,000 and 100,000 or between 500,000 and 730,000.

28. A pharmaceutical composition which comprises hyaluronic acid or a pharmaceutically acceptable salt thereof and at least one pharmacologically active substance suitable for topical administration.

29. A pharmaceutical composition according to claim 28, wherein said active substance has ophthalmological activity.

30. A pharmaceutical composition according to claim 28, wherein said active substance has dermatological activity, otorhinolaryngological, odontological, angiological, obstetrical or neurological activity.

31. A Pharmaceutical composition according to claim 28, wherein said active substance is an antibiotic, anti-infective, antiviral, antitumor, anti-inflammatory, wound healing, local anesthetic, cholinergic promoter, cholinergic antagonist, adrenergic promoter or adrenergic antagonist agent.

32. A pharmaceutical composition according to claim 28, wherein said hyaluronic acid fraction has an average molecular weight of between 30,000 and 730,000, and is substantially free of hyaluronic acid having a molecular weight of less than 30,000.

33. A Pharmaceutical composition according to claim 32, wherein said fraction has an average molecular weight of about 50,000 to about 100,000, about 250,000 to about 350,000 or about 500,000 to about 730,000.

34. A partial or a stoichiometrically neutral salt according to claim 1, wherein said pharmacologically active substance is erythromycin.

35. A pharmaceutical composition according to claim 14, wherein said pharmacologically active substance is erythromycin.

36. A pharmaceutical composition according to claim 28, wherein said pharmacologically active substance is erythromycin.

37. A method for treating ophthalmic conditions, dermatological conditions, diseases of the mucous of the oral and nasal cavities or diseases of the outer ear, comprising administering a salt of hyaluronic acid according to claim 2.

38. A method for treating ophthalmic conditions, dermatological conditions, diseases of the mucous of the oral and nasal cavities or diseases of the outer ear, comprising administering a salt of hyaluronic acid according to claim 3.

39. A method for treating ophthalmic conditions, dermatological conditions, diseases of the mucous of the oral and nasal cavities or diseases of the outer ear, comprising administering a salt of hyaluronic acid according to claim 5.

40. A method for treating ophthalmic conditions, dermatological conditions, diseases of the mucous of the oral and nasal cavities or diseases of the outer ear, comprising administering a salt of hyaluronic acid according to claim 6.

41. A method for treating ophthalmic conditions, dermatological conditions, diseases of the mucous of the oral and nasal cavities or diseases of the outer ear, comprising administering a salt of hyaluronic acid according to claim 7.

42. A method for treating ophthalmic conditions, dermatological conditions, diseases of the mucous of the oral and nasal cavities or diseases of the outer ear, comprising administering a salt of hyaluronic acid according to claim 8.

43. A method for treating ophthalmic conditions, dermatological conditions, diseases of the mucous of the oral and nasal cavities or diseases of the outer ear, comprising administering a salt of hyaluronic acid according to claim 11.

44. A method for treating ophthalmic conditions, dermatological conditions, diseases of the mucous of the oral and nasal cavities or diseases of the outer ear, comprising administering a salt of hyaluronic acid according to claim 12.

45. A method for treating ophthalmic conditions, dermatological conditions, diseases of the mucous of the oral and nasal cavities or diseases of the outer ear, comprising administering a salt of hyaluronic acid according to claim 13.

46. A method for treating ophthalmic conditions, dermatological conditions, diseases of the mucous of the oral and nasal cavities or diseases of the outer ear, comprising administering a salt of hyaluronic acid according to claim 25.

47. A method for treating ophthalmic conditions, dermatological conditions, diseases of the mucous of the oral and nasal cavities or diseases of the outer ear, comprising administering a salt of hyaluronic acid according to claim 26.

48. A method for treating ophthalmic conditions, dermatological conditions, diseases of the mucous of the oral and nasal cavities or diseases of the outer ear, comprising administering a salt of hyaluronic acid according to claim 27.

49. A method for treating ophthalmic conditions comprising administering a salt of hyaluronic acid according to claim 2.

50. A method for treating ophthalmic conditions comprising administering a salt of hyaluronic acid according to claim 3.

51. A method for treating ophthalmic conditions comprising administering a salt of hyaluronic acid according to claim 5.

52. A method for treating ophthalmic conditions comprising administering a salt of hyaluronic acid according to claim 6.

53. A method for treating ophthalmic conditions comprising administering a salt of hyaluronic acid according to claim 7.

54. A method for treating ophthalmic conditions comprising administering a salt of hyaluronic acid according to claim 8.

55. A method for treating ophthalmic conditions comprising administering a salt of hyaluronic acid according to claim 11.

56. A method for treating ophthalmic conditions comprising administering a salt of hyaluronic acid according to claim 12.

57. A method for treating ophthalmic conditions comprising administering a salt of hyaluronic acid according to claim 13.

58. A method for treating ophthalmic conditions comprising administering a salt of hyaluronic acid according to claim 25.

59. A method for treating ophthalmic conditions comprising administering a salt of hyaluronic acid according to claim 26.

60. A method for treating ophthalmic conditions comprising administering a salt of hyaluronic acid according to claim 27.

* * * * *